(12) United States Patent
Geffard

(10) Patent No.: US 10,695,437 B2
(45) Date of Patent: Jun. 30, 2020

(54) POLYCOMPLEXES OF POLY-LYSINE COMPOUNDS FOR PREVENTING AND/OR COMBATTING AMYOTROPHIC LATERAL SCLEROSIS

(71) Applicant: GEMAC, St Jean D'Illac (FR)

(72) Inventor: Michel Geffard, Talence (FR)

(73) Assignee: GEMAC, St Jean D'Illac (FR)

( * ) Notice: Subject to any disclaimer, the term of this patent is extended or adjusted under 35 U.S.C. 154(b) by 0 days.

(21) Appl. No.: 16/085,225

(22) PCT Filed: Mar. 14, 2017

(86) PCT No.: PCT/EP2017/056017
§ 371 (c)(1),
(2) Date: Sep. 14, 2018

(87) PCT Pub. No.: WO2017/157952
PCT Pub. Date: Sep. 21, 2017

(65) Prior Publication Data
US 2019/0083640 A1 Mar. 21, 2019

(30) Foreign Application Priority Data

Mar. 14, 2016 (FR) ..................................... 16 52093

(51) Int. Cl.
| | | |
|---|---|---|
| *A61K 38/00* | (2006.01) |
| *A61K 47/64* | (2017.01) |
| *A61K 38/16* | (2006.01) |
| *A61P 25/28* | (2006.01) |
| *A61K 47/12* | (2006.01) |
| *A61K 47/18* | (2017.01) |
| *A61K 31/203* | (2006.01) |
| *A61K 31/4188* | (2006.01) |
| *A61K 31/575* | (2006.01) |
| *A61K 38/06* | (2006.01) |

(52) U.S. Cl.
CPC ............ *A61K 47/645* (2017.08); *A61K 38/16* (2013.01); *A61K 47/12* (2013.01); *A61K 47/183* (2013.01); *A61P 25/28* (2018.01); *A61K 31/203* (2013.01); *A61K 31/4188* (2013.01); *A61K 31/575* (2013.01); *A61K 38/06* (2013.01)

(58) Field of Classification Search
None
See application file for complete search history.

(56) References Cited

U.S. PATENT DOCUMENTS 6,114,388 A * 9/2000 Geffard ................ A61K 47/645
514/1.3
2009/0325856 A1 12/2009 Geffard

FOREIGN PATENT DOCUMENTS

| FR | 2886153 A1 | 12/2006 |
| FR | 2905868 A1 | 3/2008 |
| WO | WO9615810 A1 | 5/1996 |

* cited by examiner

*Primary Examiner* — Jeanette M Lieb
(74) *Attorney, Agent, or Firm* — Greer, Burns & Crain, Ltd.

(57) ABSTRACT

A polycomplex comprising multiple Poly-lysine compounds, said Poly-lysine compounds being composed of at least one small molecule conjugated with a Poly-lysine. Compositions comprising the polycomplex and methods for treating an amyotrophic lateral sclerosis patient, the methods comprising administering to the patient one or more of the compositions.

5 Claims, No Drawings

POLYCOMPLEXES OF POLY-LYSINE COMPOUNDS FOR PREVENTING AND/OR COMBATTING AMYOTROPHIC LATERAL SCLEROSIS

CROSS-REFERENCE TO RELATED APPLICATIONS

This application is a U.S. national stage application of PCT/EP2017/056017 filed Mar. 14, 2017 which claims a benefit of priority from French patent application 1652093 filed Mar. 14, 2016, the entire disclosure of the both application is herein incorporated by reference.

THE TECHNICAL FIELD

This invention concerns polycomplexes of particular Poly-lysine (PLL) compounds as well as compositions including them. These polycomplexes are particularly useful as active substances of therapeutic agents, especially in preventing and/or treating Amyotrophic Lateral Sclerosis, called "ALS."

BACKGROUND

ALS is a progressive neurodegenerative disease linked to the progressive death of motor neurons, the nerve cells that control the voluntary muscles. The disease attacks the peripheral motor neurons, in direct relation with the muscles, and the central motor neurons located in the motor cortex, in the brainstem, the medulla oblongata and the spinal cord.

This systematized degeneration of the motor neurons results in numerous motor disorders such as spasms linked to muscle-tone dysregulation, increased deep tendon reflexes, muscle twitching and paralysis associated with muscle atrophy. There are few or no other signs of neurological impairment, including no sensory, oculomotor or mental disorders. Other additional symptoms accompany the motor disorders, namely: constipation, weight loss, pain, edema, vasomotor disorders, sleep and respiratory disorders.

There are three major forms of ALS determined by the site of onset of the attack of the peripheral motor neurons: the bulbar or cervical-brachial form, the upper form (central and motor cortex motor neurons) and the lower or lumbosacral form.

The spinal onset form is linked to the initial attack of the motor neurons of the spinal cord, resulting in movement disorders of the upper and lower limbs.

The bulbar form is linked to the initial attack of motor neurons of the brainstem and causes speech and swallowing disorders.

There is also a form of ALS that begins with an attack of the motor neurons of the motor cortex.

Whatever the initial form, the neurodegeneration advances progressively to a form involving multiple disabilities that influence the prognosis. In the majority of cases, death is due to respiratory failure aggravated by secondary bronchial infections. Median survival is 3-5 years in over 70% of cases.

Whatever the initial form, the neurodegeneration advances progressively to a form involving multiple disabilities that influence the prognosis. In the majority of cases, death is due to respiratory failure aggravated by secondary bronchial infections. Median survival is 3 to 5 years in more than 70% of cases.

Several genes (SOD1, ALS2, SPG20, UBQL2, C90RF72, etc.) have been identified in familial forms of ALS. However, these genetic mutations only account for a small percentage of patients with ALS. In most cases, ALS occurs sporadically. We do not note any distribution gradient around the world as is the case for other neurological diseases like Multiple Sclerosis, however we do note regions (or isolates) with higher prevalence.

There is currently no etiological treatment capable of halting the progression of ALS. The only product, Rilutek or Riluzole, is a glutamate inhibitor. It offers the patient a median survival of three to six more months, which is not very much. Furthermore, this product has numerous side effects (liver toxicity). Patient management is limited to the prevention of movement dysfunctions, help with disabilities and symptomatic treatments of the disease. Furthermore, this management requires the involvement of professionals and necessitates hospitalization and special monitoring, which is onerous for the patients and the community.

The search for effective treatments for ALS capable of controlling the progression of the disease that are easy to administer with few or no side effects is therefore a priority in human health.

For over 20 years, ALS has been the subject of numerous fundamental biomedical research projects that have established, among other things, that:
  neurodegeneration is linked to a hyperproduction of free radicals and various reactive oxygen species resulting in endogenous protein modifications, protein aggregation and neuronal death (apoptosis);
  external bacterial, viral or toxic stimuli, pollutants, intense muscle exercises and repeated electrical discharges participate in the acceleration of neurodegeneration;
  when the pathogenic processes are involved in ALS, no research has been able to identify products with inhibitory or even stabilizing activity.

Despite numerous clinical trials, conducted over more than twenty years, no effective treatment exists to date.

SUMMARY

The aim of the invention is to propose a therapeutic solution for preventing and/or combating ALS that is more effective that the few current therapeutic treatments, particularly a solution capable:
  of controlling the deleterious oxidative and free radical mechanisms, and
  of controlling the "external" "factors" or elements (bacterial, viral, toxic) involved in chronicity.

In response, the invention proposes to use polycomplexes composed of several Poly-lysine compounds, said Poly-lysine compounds consisting of at least one molecule conjugated with a Poly-lysine, said polycomplexes comprising at least the following Poly-lysine compounds:
  Cysteine-Glutaric Anhydride-Poly-lysine
  Cysteine-Reduced Glutaraldehyde-Poly-lysine
  Taurine-Glutaric Anhydride-Poly-lysine
  Taurine-Reduced Glutaraldehyde-Poly-lysine
  Methionine-Glutaric Anhydride-Poly-lysine
  Methionine-Reduced Glutaraldehyde-Poly-lysine
  Glutathione-Reduced Glutaraldehyde-Poly-lysine
  Thioctic acid-Poly-lysine.

These polycomplexes are preferably used with at least one other polycomplex composed of several Poly-lysine compounds, said Poly-lysine compounds consisting of at least one molecule conjugated with a Poly-lysine. The polycomplexes can be used together in a same composition or in different compositions but administered together in a same treatment.

The invention also relates to compositions comprising at least one polycomplex according to the invention, as well as these compositions (comprising a polycomplex or a combination of polycomplexes) for their use as active substance of a medication, particularly for preventing and/or combating ALS.

In fact, advantageously, polycomplexes as active substance of a medication according to the invention are very effective for preventing and combating ALS.

Other features and advantages will emerge from the detailed description of the invention that follows.

DETAILED DESCRIPTION

The invention therefore relates to polycomplexes composed of multiple Poly-lysine compounds, said Poly-lysine compounds consisting of at least one small molecule conjugated with a Poly-lysine.

"Polycomplex" according to the invention means a mixture or a formulation comprising multiple Poly-lysine compounds.

The polycomplexes according to the invention comprise multiple Poly-lysine compounds. A Poly-lysine compound is composed of one or more molecules conjugated with a Poly-lysine. "Molecule conjugated with a Poly-lysine" or "molecule grafted onto a Poly-lysine" means a molecule linked to a Poly-lysine by covalent or noncovalent bond (including hydrogen, ionic and Van der Waals).

Poly-lysine is a macromolecule of lysine units, preferably of linear or branched L-lysine (poly-L-lysine) where the number (n) of subunits is preferably at least 30 lysines: n≥30 lysines.

The molecules conjugated with a Poly-lysine in the Poly-lysine compounds are "small molecules," that is, molecules of small size, more specifically molecules weighing less than 1,000 daltons, and even more specifically between 75 and 500 daltons, if proteins are not involved.

The polycomplexes according to the invention preferably comprise at least the following Poly-lysine compounds:
  Cysteine-Glutaric Anhydride-Poly-lysine
  Cysteine-Reduced Glutaraldehyde-Poly-lysine
  Taurine-Glutaric Anhydride-Poly-lysine
  Taurine-Reduced Glutaraldehyde-Poly-lysine
  Methionine-Glutaric Anhydride-Poly-lysine
  Methionine-Reduced Glutaraldehyde-Poly-lysine
  Glutathione-Reduced Glutaraldehyde-Poly-lysine
  Thioctic acid-Poly-lysine.

Reduced Glutaraldehyde and Glutaric Anhydride are reactive agents that in particular allow the covalent bonding of the small molecule to the poly-lysine.

In addition, they may also comprise the following Poly-lysine compounds:
  Biotin-Poly-lysine
  Pantothenic acid-Poly-lysine
  Ascorbic acid-Poly-lysine
  Alpha tocopherol-Poly-lysine
  Retinoic acid-Poly-lysine
  Coenzyme Q10-Poly-lysine
  Spermine-Glutaric Anhydride-Poly-lysine According to a first variant, the invention relates to a polycomplex composed exclusively of the following Poly-lysine compounds:
  Cysteine-Glutaric Anhydride-Poly-lysine
  Cysteine-Reduced Glutaraldehyde-Poly-lysine
  Taurine-Glutaric Anhydride-Poly-lysine
  Taurine-Reduced Glutaraldehyde-Poly-lysine
  Methionine-Glutaric Anhydride-Poly-lysine
  Methionine-Reduced Glutaraldehyde-Poly-lysine
  Glutathione-Reduced Glutaraldehyde-Poly-lysine
  Thioctic acid-Poly-lysine.

This polycomplex is called "Polycomplex 1."

According to another variant, the invention relates to a polycomplex composed exclusively of the following Poly-lysine compounds:
  Cysteine-Glutaric Anhydride-Poly-lysine
  Cysteine-Reduced Glutaraldehyde-Poly-lysine
  Taurine-Glutaric Anhydride-Poly-lysine
  Taurine-Reduced Glutaraldehyde-Poly-lysine
  Methionine-Glutaric Anhydride-Poly-lysine
  Methionine-Reduced Glutaraldehyde-Poly-lysine
  Glutathione-Reduced Glutaraldehyde-Poly-lysine
  Thioctic acid-Poly-lysine
  Biotin-Poly-lysine
  Pantothenic acid-Poly-lysine
  Ascorbic acid-Poly-lysine
  Alpha tocopherol-Poly-lysine
  Retinoic acid-Poly-lysine
  Coenzyme Q10-Poly-lysine
  Spermine-Glutaric Anhydride-Poly-lysine.

This polycomplex is called "Polycomplex 2."

The concentration of each of the small molecules conjugated with the Poly-lysine in the polycomplex is preferably between $6 \cdot 10^{-5}$ M and $1 \cdot 10^{-4}$ M, and even more preferably between $3 \cdot 10^{-5}$ M and $2 \cdot 10^{-4}$ M. This concentration can be measured, for example, by Ultraviolet/Visible spectroscopy and by gas-phase and liquid-phase chromatography coupled to a mass spectrometer. The correlation in μg, mass of the small molecules conjugated with the Poly-lysine, is from 5 to 350 μg/ml.

The Poly-lysine compounds making up the polycomplexes are obtained in known fashion by grafting small molecules onto the Poly-lysine. The grafting method is preferably as follows:
  the small molecule is activated by an activation agent or coupling agent to form a small molecule-coupling agent intermediary;
  for certain molecules, like amino acids, this small molecule-activation agent intermediary reacts with the amino group of the lysyl residue through the formation of an amide or reduced imine bond,
  for other molecules, such as alpha-tocopherol, the carboxyl group is directly activated by ethylchloroformiate in anhydrous medium; the amide bond is made directly on the epsilon-amino group of the lysine;
  then the small molecule-Poly-lysine complex is purified;
  the final product is obtained in liquid form; it can be freeze-dried to obtain a solid form.

Activation agent or coupling agent according to the invention means: a product capable of creating a covalent bond between the —COOH or —NH$_2$ of the small molecule and the amino group, preferably the epsilon amino group, of the polypeptide. This may, for example, involve glutaraldehyde or ethylchloroformiate or glutaric anhydride.

The polycomplexes according to the invention are composed of multiple poly-lysine compounds. They may be in liquid or in solid form, that is, in powder form following freeze-drying, for example.

They can be obtained through the use of the following process:
  each Poly-lysine compound (preferably obtained as described previously) intended to be included in the polycomplex is in liquid form, and, following calculation of the concentration of small molecules, makes it possible to remove a given volume to be removed to obtain the desired final concentration and final volume in the polycomplex;

prior to removal, the Poly-Lysine compounds are stirred vigorously manually or mechanically;

the compounds are then mixed; the liquid mixture is produced at temperatures of between 18 and 22° C., by vigorous mechanical stirring, since the liquid emulsion is only slightly viscous or even not viscous; the color of the liquid mixture varies from milky white to milky yellow-orange, with variable opacity; the liquid emulsion mixture is kinetically stable;

The mixture obtained can, among other things, be frozen, then freeze-dried to obtain a powder. The powder obtained can then be mixed with excipients to obtain a pharmaceutical composition (therapeutic preparation, medication) suited to the method of application.

In fact, the polycomplexes according to the invention are intended to be administered to animals or humans. They are used as active substances of a medication and are preferably incorporated in a composition in order to constitute a therapeutic preparation or a medication.

The invention also therefore relates to compositions comprising at least one polycomplex composed of multiple Poly-lysine compounds. Said Poly-lysine compounds consisting of at least one molecule conjugated with the Poly-lysine, said polycomplex comprising at least the following Poly-lysine compounds:
  Cysteine-Glutaric Anhydride-Poly-lysine
  Cysteine-Reduced Glutaraldehyde-Poly-lysine
  Taurine-Glutaric Anhydride-Poly-lysine
  Taurine-Reduced Glutaraldehyde-Poly-lysine
  Methionine-Glutaric Anhydride-Poly-lysine
  Methionine-Reduced Glutaraldehyde-Poly-lysine
  Glutathione-Reduced Glutaraldehyde-Poly-lysine
  Thioctic acid-Poly-lysine.

According to one mode of embodiment, the composition comprises at least two polycomplexes.

According to a variant, it may, in particular, comprise at least Polycomplex 1 and/or Polycomplex 2. It may also include other polycomplexes comprising multiple Poly-lysine compounds composed of at least one molecule conjugated with the Poly-lysine.

According to another variant, the composition according to the invention may comprise at least two polycomplexes:
  at least one polycomplex chosen from Polycomplex 1 and Polycomplex 2,
  and at least one polycomplex comprising multiple Poly-lysine compounds composed of at least one molecule conjugated with the Poly-lysine, said polycomplex being chosen from the following polycomplexes:
    Polycomplex 3 composed exclusively of the following Poly-lysine compounds:
      Biotin-Poly-lysine
      Coenzyme Q10-Poly-lysine
      Retinoic acid-Poly-lysine
      Thioctic acid-Poly-lysine
      Pantothenic acid-Poly-lysine
      Ascorbic acid-Poly-lysine
      Alpha tocopherol-Poly-lysine
      Glutathione-Reduced Glutaraldehyde-Poly-lysine
      Oleic acid-Poly-lysine
    Polycomplex 4 composed exclusively of the following Poly-lysine compounds:
      Oleic acid-Poly-lysine
      Palmitoleic acid-Poly-lysine
      Linoleic acid-Poly-lysine
      Cholesterol-Poly-lysine
      Lauric acid-Poly-lysine
      Palmitic acid-Poly-lysine
      Myristic acid-Poly-lysine
      Thioctic acid-Poly-lysine
    Polycomplex 5 composed exclusively of the following Poly-lysine compounds:
      Lauric acid-Poly-lysine
      Lactic acid-Poly-lysine
      Pyruvic acid-Poly-lysine
    Polycomplex 6 composed exclusively of the following Poly-lysine compounds:
      Acetic acid-Poly-lysine
      Butyric acid-Poly-lysine
      Lactic acid-Poly-lysine
      Propionic acid-Poly-lysine
      Pyruvic acid-Poly-lysine.
    Polycomplex 7 composed exclusively of the following Poly-lysine compounds:
      Retinoic acid-Poly-lysine
      Alpha tocopherol-Poly-lysine
      Ascorbic acid-Poly-lysine
      Coenzyme Q10-Poly-lysine
      Spermine-Glutaric Anhydride-Poly-lysine.
      Cysteine-Glutaric Anhydride-Poly-lysine
      Cysteine-Reduced Glutaraldehyde-Poly-lysine
      Methionine-Glutaric Anhydride-Poly-lysine
      Methionine-Reduced Glutaraldehyde-Poly-lysine
      Taurine-Glutaric Anhydride-Poly-lysine
      Taurine-Reduced Glutaraldehyde-Poly-lysine
    Polycomplex 8 composed exclusively of the following Poly-lysine compounds:
      Oleic acid-Poly-lysine
      Farnesyl cysteine-Poly-lysine
      Cholesterol-Poly-lysine
      Palmitoleic acid-Poly-lysine
      Palmitic acid-Poly-lysine
      Linoleic acid-Poly-lysine
      Myristic acid-Poly-lysine
      Thioctic acid-Poly-lysine
      Azelaic acid-Poly-lysine
    Polycomplex 9 composed exclusively of the following Poly-lysine compounds:
      Oleic acid-Poly-lysine
      Thioctic acid-Poly-lysine
      Retinoic acid-Poly-lysine
      Coenzyme Q10-Poly-lysine
    Polycomplex 10 composed exclusively of the following Poly-lysine compounds:
      Lauric acid-Poly-lysine
      Oleic acid-Poly-lysine
      Palmitoleic acid-Poly-lysine
      Linoleic acid-Poly-lysine
      Cholesterol-Poly-lysine
      Palmitic acid-Poly-lysine
      Myristic acid-Poly-lysine
      Thioctic acid-Poly-lysine
      Coenzyme Q10-Poly-lysine
      Retinoic acid-Poly-lysine
      Pyruvic acid-Poly-lysine.
      Glutathione-Reduced Glutaraldehyde-Poly-lysine
      Cysteine-Glutaric Anhydride-Poly-lysine
      Cysteine-Reduced Glutaraldehyde-Poly-lysine
      Taurine-Glutaric Anhydride-Poly-lysine
      Taurine-Reduced Glutaraldehyde-Poly-lysine Methionine-Glutaric Anhydride-Poly-lysine
Methionine-Reduced Glutaraldehyde-Poly-lysine
Polycomplex 11 composed exclusively of the following Poly-lysine compounds:
Oleic acid-Poly-lysine
Azelaic acid-Poly-lysine
Farnesyl cysteine-Poly-lysine
Thioctic acid-Poly-lysine
Palmitic acid-Poly-lysine
Methionine-Glutaric Anhydride-Poly-lysine
Taurine-Glutaric Anhydride-Poly-lysine
Gamma-aminobutyric acid-Reduced Glutaraldehyde-Poly-lysine
Polycomplex 12 composed exclusively of the following Poly-lysine compounds:
5-hydroxytryptamine-Glutaric Anhydride-Poly-lysine
5-hydroxytryptophane-Glutaric Anhydride-Poly-lysine
LDopa-Glutaric Anhydride-Poly-lysine
Methionine-Reduced Glutaraldehyde-Poly-lysine
Taurine-Reduced Glutaraldehyde-Poly-lysine
Gamma-aminobutyric acid-Reduced Glutaraldehyde-Poly-lysine According to a preferred variant, the composition comprises at least the following polycomplexes:
at least one polycomplex chosen from Polycomplex 1 and Polycomplex 2, potentially at least Polycomplex 1 and Polycomplex 2,
and at least Polycomplex 3.

According to another preferred variant, the composition comprises at least the following polycomplexes:
at least one polycomplex chosen from Polycomplex 1 and Polycomplex 2, potentially at least Polycomplex 1 and Polycomplex 2, and at least Polycomplex 3, Polycomplex 4, Polycomplex 5 and Polycomplex 6.

For a judicious therapeutic choice, the polycomplex or polycomplexes containing antioxidants and/or free radical scavengers are preferably present in the composition at a molar concentration at least 2.5 times higher compared to the other polycomplexes not containing antioxidants and/or free radical scavengers. The aim is to administer at least 2.5 times more antioxidants and free radical scavengers than fatty acids or other compounds (lipophile derivatives, amino acids and derivatives).

In particular, in the variant comprising at least Polycomplex 1 and/or 2, and Polycomplexes 3, 4, 5 and 6, the quantity of Polycomplexes 1 and/or 2 and 3 together (these polycomplexes comprising antioxidants and/or free radical scavengers), is at least 2.5 times higher than the quantity of Polycomplexes 4, 5 and 6 together.

The concentration of each of the small molecules in the polycomplexes present is preferably between $6 \cdot 10^{-5}$ and $1 \cdot 10^{-4}$ mol/L, even more preferably between $3.10^{-5}$ and $2 \cdot 10^{-4}$ mol/L.

The compositions according to the invention may be in any form suited to a therapeutic administration in humans or animals, particularly sublingual tablets, capsules, drinkable solution, injectable solution, pressurized metered dose inhaler, tablet, capsules, ointment, cream, suppository or patches suited to cutaneous administration. Preferably, the compositions according to the invention are in the form of gastro-resistant capsules or tablets suited to sublingual administration, preferably sublingual tablets.

The polycomplexes present in the compositions are active substances that have a therapeutic effect.

In addition to the polycomplex(es) according to the invention, the compositions may also comprise other components, including excipients that do not have any therapeutic effect, such as, for example, mannitol, starch, microcrystalline cellulose, polyethylene glycol, talc, magnesium stearate, silica and other excipients necessary to the galenic formulation of the tablet. If the composition is in a form suited to injection, it preferably comprises isotonic saline.

Considering that the polycomplexes according to the invention have a therapeutic effect, the invention therefore relates to these polycomplexes and/or compositions for their preventive and/or curative therapeutic applications, particularly for the prevention and/or the treatment of ALS.

In particular, the invention relates to compositions comprising at least one polycomplex according to the invention for their application as medication.

According to one mode of embodiment, the invention relates to a composition comprising Polycomplex 1, for its use as medication in combination with at least one composition comprising at least one polycomplex chosen from the following polycomplexes:
Polycomplex 2,
Polycomplex 3,
Polycomplex 4,
Polycomplex 5,
Polycomplex 6,
Polycomplex 8,
Polycomplex 9.

According to another mode of embodiment, the invention relates to a composition comprising Polycomplex 2, for its use as medication in combination with at least one composition comprising at least one polycomplex chosen from the following polycomplexes:
Polycomplex 3,
Polycomplex 4,
Polycomplex 5,
Polycomplex 6,
Polycomplex 7,
Polycomplex 8,
Polycomplex 10,
Polycomplex 11,
Polycomplex 12.

According to preferred variant, the invention relates to a composition comprising Polycomplex 1 and/or 2, for its use as medication in combination with at least one composition comprising at least Polycomplex 3.

According to another preferred variant, the invention relates to a composition comprising Polycomplex 1 and/or 2 (or a composition comprising Polycomplex 1 and a composition comprising Polycomplex 2) for its use as medication in combination with at least Polycomplex 3, Polycomplex 4, Polycomplex 5 and Polycomplex 6, said polycomplexes 3, 4, 5 and 6 being formulated in a same composition or in several different compositions.

For a judicious therapeutic choice, the polycomplex or polycomplexes containing antioxidants and/or free radical scavengers are preferably used in the composition in a quantity at least 2.5 times greater in molar concentration compared to the other polycomplexes not containing antioxidants and/or free radical scavengers. The aim is to administer at least 2.5 times more antioxidants and free radical scavengers than fatty acids, derivatives and/or amino acids and derivatives.

In particular, in the variant consisting in administering at least Polycomplex 1 and/or 2, and Polycomplexes 3, 4, 5 and 6, the quantity of Polycomplexes 1 and/or 2 and 3 together (these polycomplexes comprising antioxidants and/or free radical scavengers) is at least 2.5 times higher than the quantity of Polycomplexes 4, 5 and 6 together.

The concentration of each of the small molecules in the polycomplexes is preferably between $6 \cdot 10^{-5}$ and $1 \cdot 10^{-4}$ mol/L, more preferably still between $3 \cdot 10^{-5}$ and $2 \cdot 10^{-4}$ mol/L.

The polycomplexes and compositions according to the invention are particularly effective in the context of preventing and treating ALS. They make it possible to completely or partially control the disease and to improve the ALS functional rating scale scores for speech, salivation, swallowing, writing, the ability to cut food and hold utensils, the ability to dress and wash, the ability to roll over in bed and to adjust the sheets, walking, the ability to climb stairs and breathing.

The vitamins, antioxidants and amino acids on the Poly-lysine contained in the polycomplexes according to the invention make it possible to combat the radical mechanisms responsible for neuronal death.

The presence of short, medium and long-chain fatty acids bonded to the Poly-lysine provides antibacterial, antifungal and virucidal activities but also immunomodulating and toxin scavenging activities. These compounds have an etiological role with regard to chronicity factors.

Preferably, the compositions according to the invention are in solid form (sublingual tablet, capsule, etc.). Each 100 mg tablet constitutes a therapeutic unit. The polycomplex or polycomplexes and the composition or compositions is (are) then formed and administered so that:
- the daily dose of grafted small molecules varies from 15 to 90 µg per day, and
- each Poly-lysine compound represents 0.2 to 2.5 mg per therapeutic unit administered.

According to a particularly suitable mode of embodiment, the total quantity of polycomplexes administered to a patient over a week, that is, all the polycomplexes (1 and/or 2 and the potential other polycomplexes administered in association with Polycomplex(es) 1 and/or 2 in a same composition or in one or more other composition(s)) is greater than or equal to 210 mg. This quantity is independent of the weight of the patient to whom it is administered.

The invention will now be illustrated by examples of polycomplexes and medicinal compositions including them, and by results of trials conducted on volunteer ALS patients.

Examples of Polycomplexes According to the Invention

Method for Producing the Polycomplexes

The polycomplexes of the examples are obtained according to the following method (from Poly-lysines obtained through a known grafting method as described in this application):
- recovery of the indicated quantities of each Poly-lysine compound in liquid form;
- obtaining for each Poly-lysine compound with its small molecules concentration calculation, a given volume to be removed to achieve the desired final concentration and the final desired volume of polycomplex, namely 1000 to 10,000 ml;
- prior to removal, the Poly-lysine compounds are stirred manually or mechanically;
- the Poly-lysine compounds in liquid phase are then mixed after pipetting during magnetic stirring;
- the emulsion of the liquid mixture is carried out at temperatures of between 18 and 22° C., by vigorous mechanical stirring at 60 rpm;
- the mixture obtained is frozen, then freeze-dried to obtain a powder.

These products do not present any risk of toxicity or side effects. Animal experimentation has confirmed the absence of toxicity and adverse reactions. They are intended to be incorporated in a composition.

Example 1: Example of Polycomplex 1 According to the Invention

| Poly-L-Lysine compounds | Final concentration (in mol/L) Of grafted small molecules |
|---|---|
| CYSTEINE - Glutaric Anhydride - PLL | $1 \times 10^{-4}$ |
| CYSTEINE - Reduced Glutaraldehyde - PLL | $1 \times 10^{-4}$ |
| TAURINE - Glutaric Anhydride - PLL | $1 \times 10^{-4}$ |
| TAURINE - Reduced Glutaraldehyde - PLL | $1 \times 10^{-4}$ |
| METHIONINE - Glutaric Anhydride - PLL | $1 \times 10^{-4}$ |
| METHIONINE - Reduced Glutaraldehyde - PLL | $1 \times 10^{-4}$ |
| GLUTATHION - Reduced Glutaraldehyde - PLL | $1 \times 10^{-4}$ |
| THIOCTIC ACID - PLL | $1 \times 10^{-4}$ |

Weight: 2.3 mg/ml (or tablet)

Example 2: Example of Polycomplex 2 According to the Invention

| Poly-L-Lysine compounds | Final concentration (in mol/L) Of grafted small molecules |
|---|---|
| BIOTIN - PLL | $6 \times 10^{-5}$ |
| PANTOTHENIC ACID - PLL | $6 \times 10^{-5}$ |
| ASCORBIC ACID - PLL | $6 \times 10^{-5}$ |
| ALPHA TOCOPHEROL - PLL | $6 \times 10^{-5}$ |
| GLUTATHION - Reduced Glutaraldehyde - PLL | $1 \times 10^{-4}$ |
| THIOCTIC ACID - PLL | $1 \times 10^{-4}$ |
| RETINOIC ACID - PLL | $6 \times 10^{-5}$ |
| COENZYME Q10 - PLL | $6 \times 10^{-5}$ |
| SPERMINE Glutaric Anhydride - PLL | $6 \times 10^{-5}$ |
| CYSTEINE - Glutaric Anhydride - PLL | $6 \times 10^{-5}$ |
| CYSTEINE - Reduced Glutaraldehyde - PLL | $6 \times 10^{-5}$ |
| TAURINE - Glutaric Anhydride - PLL | $6 \times 10^{-5}$ |
| TAURINE - Reduced Glutaraldehyde - PLL | $6 \times 10^{-5}$ |
| METHIONINE - Glutaric Anhydride - PLL | $6 \times 10^{-5}$ |
| METHIONINE - Reduced Glutaraldehyde - PLL | $1 \times 10^{-4}$ |

Weight: 2.5 mg/ml (or tablet)

Examples of Polycomplexes That Can Be Combined with the Polycomplexes According to the Invention in a Composition or at Time of Treatment Method for Producing the Polycomplexes The polycomplexes of examples 3 to 12 are obtained according to the following method (from Poly-lysines obtained by a known grafting method as described in this application):
- recovery of the indicated quantities of each Poly-lysine compound in liquid form;
- obtaining for each Poly-lysine compound with its small molecules concentration calculation, a given volume to be removed to achieve the desired final concentration and the final desired volume of polycomplex, namely 1000 to 10,000 ml;
- prior to removal, the Poly-lysine compounds are stirred manually or mechanically;
- the Poly-lysine compounds in liquid phase are then mixed after pipetting during magnetic stirring;

the emulsion of the liquid mixture is carried out at temperatures of between 18 and 22° C., by vigorous mechanical stirring at 60 rpm;

the mixture obtained is frozen, then freeze-dried to obtain a powder.

These products do not present any risk of toxicity or side effects. They are intended to be incorporated in a composition.

Example 3: Example of Polycomplex 3

| Poly-L-Lysine compounds | Final concentration (in mol/L) Of grafted small molecules |
|---|---|
| BIOTIN - PLL | $3 \times 10^{-5}$ |
| COENZYME Q10 - PLL | $3 \times 10^{-5}$ |
| RETINOIC ACID - PLL | $3 \times 10^{-5}$ |
| THIOCTIC ACID - PLL | $3 \times 10^{-5}$ |
| PANTOTHENIC ACID - PLL | $3 \times 10^{-5}$ |
| ASCORBIC ACID - PLL | $3 \times 10^{-5}$ |
| ALPHA-TOCOPHEROL - PLL | $3 \times 10^{-5}$ |
| GLUTATHION Reduced Glutaraldehyde - PLL | $3 \times 10^{-5}$ |
| OLEIC ACID - PLL | $6 \times 10^{-5}$ |

Weight: 0.7 mg/ml (or tablet)

Example 4: Example of Polycomplex 4

| Poly-L-Lysine compounds | Final concentration (in mol/L) Of grafted small molecules |
|---|---|
| OLEIC ACID - PLL | $3 \times 10^{-5}$ |
| PALMITOLEIC ACID - PLL | $3 \times 10^{-5}$ |
| LINOLEIC ACID - PLL | $3 \times 10^{-5}$ |
| CHOLESTEROL - PLL | $3 \times 10^{-5}$ |
| LAURIC ACID - PLL | $3 \times 10^{-5}$ |
| PALMITIC ACID - PLL | $3 \times 10^{-5}$ |
| MYRISTIC ACID - PLL | $3 \times 10^{-5}$ |
| THIOCTIC ACID - PLL | $3 \times 10^{-5}$ |

Weight: 0.4 mg/ml (or tablet)

Example 5: Example of Polycomplex 5

| Poly-L-Lysine compounds | Final concentration (in mol/L) Of grafted small molecules |
|---|---|
| LAURIC ACID-PLL | $5 \times 10^{-4}$ |
| LACTIC ACID-PLL | $2 \times 10^{-4}$ |
| PYRUVIC ACID-PLL | $2 \times 10^{-4}$ |

Weight: 0.8 mg/ml (or tablet)

Example 6: Example of Polycomplex 6

| Poly-L-Lysine compounds | Final concentration (mol/L) Of grafted small molecules |
|---|---|
| ACETIC ACID-PLL | $3 \times 10^{-5}$ |
| BUTYRIC ACID-PLL | $3 \times 10^{-5}$ |
| LACTIC ACID-PLL | $3 \times 10^{-5}$ |
| PROPIONIC ACID-PLL | $3 \times 10^{-5}$ |
| PYRUVIC ACID-PLL | $3 \times 10^{-5}$ |

Weight: 0.04 mg/ml (or tablet)

Example 7: Example of Polycomplex 7

| Poly-L-Lysine compounds | Final concentration (mol/L) Of grafted small molecules |
|---|---|
| RETINOIC ACID-PLL | $3 \times 10^{-5}$ |
| ALPHA-TOCOPHEROL-PLL | $3 \times 10^{-5}$ |
| ASCORBIC ACID-PLL | $3 \times 10^{-5}$ |
| COENZYME Q10-PLL | $3 \times 10^{-5}$ |
| SPERMINE-Glutaric Anhydride-PLL | $3 \times 10^{-5}$ |
| CYSTEINE-Glutaric Anhydride-PLL | $3 \times 10^{-5}$ |
| CYSTEINE-Reduced Glutaraldehyde-PLL | $3 \times 10^{-5}$ |
| TAURINE-Glutaric Anhydride-PLL | $3 \times 10^{-5}$ |
| TAURINE-Reduced Glutaraldehyde-PLL | $3 \times 10^{-5}$ |
| METHIONINE-Glutaric Anhydride-PLL | $3 \times 10^{-5}$ |
| METHIONINE-Reduced Glutaraldehyde-PLL | $3 \times 10^{-5}$ |

Weight: 1 mg/ml (or tablet)

Example 8: Example of Polycomplex 8

| Poly-L-Lysine compounds | Final concentration (in mol/L) Of grafted small molecules |
|---|---|
| OLEIC ACID-PLL | $1 \times 10^{-4}$ |
| FARNESYL CYSTEINE-PLL | $1 \times 10^{-4}$ |
| CHOLESTEROL-PLL | $3 \times 10^{-5}$ |
| PALMITOLEIC ACID-PLL | $6 \times 10^{-5}$ |
| LINOLEIC ACID-PLL | $6 \times 10^{-5}$ |
| AZELAIC ACID-PLL | $6 \times 10^{-5}$ |
| PALMITIC ACID-PLL | $6 \times 10^{-5}$ |
| MYRISTIC ACID-PLL | $6 \times 10^{-5}$ |
| THIOCTIC ACID-PLL | $6 \times 10^{-5}$ |

Weight: 0.9 mg/ml (or tablet)

Example 9: Example of Polycomplex 9

| Poly-L-Lysine compounds | Final concentration (in mol/L) Of grafted small molecules |
|---|---|
| OLEIC ACID-PLL | $6 \times 10^{-5}$ |
| THIOCTIC ACID-PLL | $3 \times 10^{-5}$ |
| RETINOIC ACID-PLL | $3 \times 10^{-5}$ |
| COENZYME Q10-PLL | $3 \times 10^{-5}$ |

Weight: 0.2 mg/ml (or tablet)

Example 10: Example of Polycomplex 10

| Poly-L-Lysine compounds | Final concentration (in mol/L) Of grafted small molecules |
|---|---|
| LAURIC ACID-PLL | $6 \times 10^{-5}$ |
| OLEIC ACID-PLL | $6 \times 10^{-5}$ |
| CHOLESTEROL-PLL | $6 \times 10^{-5}$ |
| PALMITOLEIC ACID-PLL | $6 \times 10^{-5}$ |
| LINOLEIC ACID-PLL | $6 \times 10^{-5}$ |
| PALMITIC ACID-PLL | $6 \times 10^{-5}$ |
| MYRISTIC ACID-PLL | $6 \times 10^{-5}$ |
| THIOCTIC ACID-PLL | $6 \times 10^{-5}$ |
| PYRUVIC ACID-PLL | $1 \times 10^{-4}$ |
| COENZYME Q10-PLL | $3 \times 10^{-5}$ |
| RETINOIC ACID-PLL | $3 \times 10^{-5}$ |
| GLUTATHION-Reduced Glutaraldehyde-PLL | $3 \times 10^{-5}$ |
| CYSTEINE-Glutaric Anhydride-PLL | $3 \times 10^{-5}$ |
| CYSTEINE-Reduced Glutaraldehyde-PLL | $3 \times 10^{-5}$ |
| TAURINE-Glutaric Anhydride-PLL | $3 \times 10^{-5}$ |
| TAURINE-Reduced Glutaraldehyde-PLL | $3 \times 10^{-5}$ |
| METHIONINE-Glutaric Anhydride-PLL | $3 \times 10^{-5}$ |
| METHIONINE-Reduced Glutaraldehyde-PLL | $3 \times 10^{-5}$ |

Weight: 2 mg/ml (or tablet)

Example 11: Example of Polycomplex 11

| Poly-L-Lysine compounds | Final concentration (in mol/L) Of grafted small molecules |
|---|---|
| OLEIC ACID-PLL | $6 \times 10^{-5}$ |
| AZELAIC ACID-PLL | $6 \times 10^{-5}$ |
| FARNESYL CYSTEINE-PLL | $3 \times 10^{-5}$ |
| THIOCTIC ACID-PLL | $3 \times 10^{-5}$ |
| PALMITIC ACID-PLL | $3 \times 10^{-5}$ |
| METHIONINE-Glutaric Anhydride-PLL | $3 \times 10^{-5}$ |
| TAURINE-Glutaric Anhydride-PLL | $3 \times 10^{-5}$ |
| GAMMA-AMINOBUTYRIC ACID-Reduced Glutaraldehyde-PLL | $3 \times 10^{-5}$ |

Weight: 0.6 mg/ml (or tablet)

Example 12: Example of Polycomplex 12

| Poly-L-Lysine compounds | Final concentration (in mol/L) Of grafted small molecules |
|---|---|
| 5-HYDROXYTRYPTAMINE-Glutaric Anhydride-PLL | $1 \times 10^{-4}$ |
| 5-HYDROXYTRYPTOPHANE-Glutaric Anhydride-PLL | $1 \times 10^{-4}$ |
| LDOPA-Glutaric Anhydride-PLL | $1 \times 10^{-4}$ |
| METHIONINE-Reduced Glutaraldehyde-PLL | $1 \times 10^{-4}$ |
| TAURINE-Reduced Glutaraldehyde-PLL | $1 \times 10^{-4}$ |
| GAMMA-AMINOBUTYRIC ACID-Reduced Glutaraldehyde-PLL | $1 \times 10^{-4}$ |

Weight: 1.5 mg/ml (or tablet)

Examples of Compositions According to the Invention

Example 13: Example of Composition Corresponding to a Therapeutic Unit (Sublingual Tablet) Comprising Polycomplex 1 Only and the Excipients The composition of example 13 is as follows:

| Components | Content (%) |
|---|---|
| Mannitol (for direct compression) | 58.7 |
| Pregelatinized starch | 16 |
| Microcrystalline cellulose | 10 |
| PEG | 5 |
| PVP K30 | 2.5 |
| Talc | 2 |
| Magnesium stearate | 1.5 |
| Amorphous silica | 1 |
| Levilite | 1 |
| Total excipients | 97.7 |
| Polycomplex 1 | 2.3 |
| Total | 100 |

The percentage is given by weight of dry matter.

The composition according to the invention is in the form of a 100 mg sublingual tablet.

The powder containing the active ingredients and the excipients is compressed to form the sublingual tablet so that it can dissolve in 3 to 10 minutes. The active ingredients pass through the sublingual vascular wall directly and are thus distributed by the blood to the lesions with the aim of neutralizing the radical species and thus preventing endogenous protein modifications and therefore neuronal death.

The dosage for this tablet prescribed alone is 2 tablets, 3 times a day, every other day, which corresponds to an administration of 225 mg per month of antioxidants and free radical scavengers.

Example 14: Example of Composition Corresponding to a Therapeutic Unit (Sublingual Tablet) Comprising Polycomplex 2 Only with Excipients The composition of example 14 is as follows:

| Components | Content (%) |
|---|---|
| Mannitol (for direct compression) | 57 |
| Pregelatinized starch | 16 |
| Microcrystalline cellulose | 10 |
| PEG | 5 |
| PVP K30 | 2.5 |
| Talc | 2 |
| Magnesium stearate | 1.5 |
| Amorphous silica | 1 |
| Levilite | 1 |
| Total excipients | 97 |
| Polycomplex 2 | 2 |
| Total | 100 |

The percentage is given by weight of dry matter.

The composition according to is in the form of a 100 mg sublingual tablet

The powder containing the active ingredients and the excipients is compressed to form the sublingual tablet so that it can dissolve in 3 to 10 minutes. The active ingredients pass through the sublingual vascular wall directly and are thus distributed by the blood to the lesions with the aim of neutralizing the radical species and thus preventing endogenous protein modifications and therefore neuronal death.

The dosage for this tablet prescribed alone is 2 tablets, 3 times a day, two days out of three, which corresponds to an administration of 276 mg per month of antioxidants and free radical scavengers.

Example 15: Example of Association of Polycomplex 1 and Polycomplex 2

The compositions of example 13 and of example 14 may be used together in a same treatment for a synergistic effect.
The dosage for this example is as follows:
Day 1: Polycomplex 1 (composition of example 13): 2 tablets, 3 times a day,
Day 2: Polycomplex 2 (composition of example 14): 2 tablets, 3 times a day,
Day 3: nothing
Day 4: same dosage as Day 1
Day 5: same dosage as Day 2
Day 6: same dosage as Day 3
Etc.

The quantity of antioxidants and of free radical scavengers administered, which corresponds to an administration of 288 mg per month.

Example 16: Example of Association of Polycomplexes 1 and 2 with Other Polycomplexes The compositions of examples 13 and 14 are used for this example as well as identical compositions concerning the excipients but comprising instead of Polycomplex 1 or 2, one of Polycomplexes 3 to 5 (examples 3 to 5).
The dosage for this example 10 is as follows:
Day 1: Polycomplex 2 (composition of example 14): 2 tablets, 3 times a day,
Day 2: Polycomplex 3 in a composition: 2 tablets, 2 times a day, +Polycomplex 5 in a composition: 2 tablets, 3 times a day,
Day 3: Polycomplex 1 (composition of example 13): 2 tablets, 3 times a day,
Day 4: Polycomplex 2 (composition of example 14): 2 tablets, 3 times a day +Polycomplex 5: 2 tablets, 3 times a day,
Day 5: nothing,
Day 6: same dosage as Day 1,
Day 7: same dosage as Day 2,
Day 8: same dosage as Day 3,
Day 9: same dosage as Day 4,
Day 10: same dosage as Day 5,
Etc.
Total mg per month:
Of polycomplex 1: 82.8 mg
Of polycomplex 2: 144 mg per month
Of polycomplex 3: 16.8 mg per month
Of polycomplex 5: 57.6 mg per month
Total mg of antioxidants and free radical scavengers=243.6 mg per month,
Total fatty acid plus amino acid=57.6 mg per month
Ratio between antioxidants+free radical scavengers/fatty acids+amino acids=4.23.
Trials Demonstrating the Effectiveness of the Invention
Treatment/Effectiveness Evaluation Protocol The polycomplexes and compositions according to the invention are particularly effective in the context of preventing and treating ALS. They allow control and improvement of ALS functional rating scale scores for both motor mechanisms and language.

The treatment protocols are detailed at the start of each of the studies.

Volunteer patients were followed up at their request by neurologists or physicians. The therapeutic activity of the polycomplexes was evaluated from a clinical standpoint using the ALSQ-40 score. This validated tool evaluates the functional capacities of patients with ALS (Sancho and Boisson, 2006).

This score is established based on a scale of 10 items:
a. Speech
b. Salivation
c. Swallowing
d. Writing
e. Ability to cut food and hold utensils (patients not requiring feeding tube)
e'. Ability to cut food and hold utensils (patients requiring a feeding tube); item e. or e'. is taken into consideration.
f. Ability to dress and wash
g. Ability to roll over in bed and to adjust the sheets
h. Walking
i. Ability to climb stairs
j. Breathing Each item ranges between 0 and 4. The value obtained at time t of evolution gives the patient's functionality at the time of the patient's clinical exam. The closer the score is to 40, the more normal the functions.

The R reference corresponds to the median worldwide reference curve of ALS progression. The speed of progression of the disease corresponds to a functional loss of −0.769 point/month.

At the patient's first evaluation, the starting point of the reference curve is established. This curve makes it possible to situate the patient's score (M) at the time of the exam and to track its evolution over time. It also makes it possible to evaluate the effectiveness of the therapies.

| Interpretation table | | | |
|---|---|---|---|
| Mean individual speed < or equal to −0.769 | Mean individual speed between −0.769 and 0 | Mean individual speed = 0 | Mean individual speed > 0 |
| Progression of the disease | Deceleration of the disease | Stabilization of the disease | Reversal of the progression of the disease |
| No therapeutic effect of the treatment | Start of effectiveness of the treatment | Effective treatment | Very effective treatment with repair |

Study 1

This first study relates to the evaluation of the effectiveness of the treatment using preparations of polycomplexes containing Poly-lysine compounds in 13 volunteer patients with ALS, including 6 patients undergoing treatment (between 4 and 16 months).

The study of 6 new patients rounded out the results.

The durations of treatment using preparations of polycomplexes containing Poly-lysine compounds are between 4 months and 91 months (7.5 years). To compensate for this variability, an adapted valuation method was used to compare the patients with one another and to evaluate the average effectiveness of the treatment using preparations of polycomplexes containing Poly-lysine compounds on all 19 patients.

The dosage for this study is as follows (with the understanding that the polycomplexes are administered in compositions with the excipients of compositions of examples 13 and 14 and that the polycomplexes are those of the examples):
Day 1: Polycomplex 2: 1 tablet, 3 times a day,
Day 2: Polycomplex 7: 1 tablet, 3 times a day, +Polycomplex 8: 1 tablet, 3 times a day,
Day 3: Polycomplex 2: 1 tablet, 3 times a day,
Day 4: Polycomplex 3: 2 tablets, 3 times a day,
Day 5: nothing,
Day 6: same dosage as Day 1,
Day 7: same dosage as Day 2,
Day 8: same dosage as Day 3,
Day 9: same dosage as Day 4,
Day 10: same dosage as Day 5,
Etc.

The treatment protocol is presented in the following table:

| Treatment protocol | | | | | | | | | | | | | | | | | |
|---|---|---|---|---|---|---|---|---|---|---|---|---|---|---|---|---|---|
| Category | | | | | | | | | | | | | | | | | |
| 1 | | | | 1 | | | | 2 | | | | 1 | | | | | |
| Product | | | | | | | | | | | | | | | | | |
| Polycomplex 2 | | | | Polycomplex 7 | | | | Polycomplex 8 | | | | Polycomplex 3 | | | | | |
| mg | | | | | | | | | | | | | | | | | |
| 2.5 | | | | 1 | | | | 0.9 | | | | 0.7 | | | | Total | |
| | M | Noon | E | Total | M | Noon | E | Total | M | Noon | E | Total | M | Noon | E | Total | tab/day |
| Day 1 | 1 | 1 | 1 | 3 | — | — | — | 0 | — | — | — | 0 | — | — | — | 0 | 3 |
| Day 2 | — | — | — | 0 | 1 | 1 | 1 | 3 | 1 | 1 | 1 | 3 | — | — | — | 0 | 6 |
| Day 3 | 1 | 1 | 1 | 3 | — | — | — | 0 | — | — | — | 0 | — | — | — | 0 | 3 |
| Day 4 | — | — | — | 0 | — | — | — | 0 | — | — | — | 0 | 2 | 2 | 2 | 6 | 6 |
| Day 5 | — | — | — | 0 | — | — | — | 0 | — | — | — | 0 | — | — | — | 0 | 0 |
| Total tab/month | | 36 | | | | 18 | | | | 18 | | | | 36 | | | 108 | |
| Total mg/month | | 72 | | | | 13.5 | | | | 18 | | | | 25.2 | | | 128.7 | |
| | | | | | | | | | | | | | Total AO + Sc (mg) | | | 110.7 | |
| | | | | | | | | | | | | | Total AO + Sc (mg) | | | 18 | |
| | | | | | | | | | | | | | AO + Sc/FA + AA ratio | | | 6.15 | |

Legend:
tab = tablet,
M = morning,
E = evening,
mg = milligram of polycomplex,
AO = Antioxidants,
FA = Fatty acids,
AA = Amino acids,
Sc = Scavengers (free radical scavengers),
category 1 = AO + Sc,
category 2 = AA + FA The individual ALSQ-40 (ALS functional progression scale) score shows fluctuations over time.

To evaluate the overall effect of the treatment using preparations of polycomplexes containing Poly-lysine compounds for each patient, we determine the straight line of mean individual evolution of the ALSQ-40 score over time whose slope corresponds to the mean individual speed of evolution of the ALSQ-40 score. The scatter plot is adjusted for the calculation.

This mean individual speed of evolution of the ALSQ-40 score is the evaluation criterion used to evaluate the overall effect of the treatment using preparations of polycomplexes containing Poly-lysine compounds.

The results are presented in the tables below:

| Evolution of functional capacities (ALSQ40) | Study of 13 patients | Study with 6 new patients |
|---|---|---|
| Aggravation | 15% | 17% |
| Deceleration | 54% | 33% |
| Stabilization | 8% | 17% |
| Reversal of the disease = Improvement | 23% | 33% |
| Favorable evolution rate | 85% | 83% |

Percentage of the evolution of the patients based on the ALSQ40 score taking into account the functional capacities of each patient.
A favorable evolution of between 83 and 85% is noted.

| Evolution of functional capacities (ALSQ40) | Study of 13 patients | Study with 6 new patients |
|---|---|---|
| Mean speed of the score for all of the patients | −0.391 | −0.419 |
| Mean speed of the worldwide reference score | −0.769 point/month | |
| Rate of deceleration of loss of functional capacities | 49.15% | 45.51% |
| Gain in months | 50.3 | 43.5 |
| Gain in years | 4.19 | 3.63 |

A gain in survival compounds is of 3.6 to 4.2 years on average owing to the preparations of polycomplexes containing Poly-lysine compounds is noted.

Analysis of these data confirms the effectiveness of the invention.

We observe a favorable evolution of clinical condition in over 83% of the patients treated with preparations of polycomplexes containing Poly-lysine compounds, expressed, depending on the case, either by a deceleration of the loss of functional capacities or by a stabilization of functional capacities, or by an improvement in functional capacities.

The gain for patients is 4 years on average, which represents a survival time that is virtually doubled compared to the worldwide reference.

Study 2

The aim of this study was to demonstrate the effectiveness of preparations of polycomplexes containing Poly-lysine compounds in volunteer patients with ALS.

The dosage for this study is as follows (with the understanding that the polycomplexes are administered in compositions with the excipients of the compositions of examples 13 and 14 and that the polycomplexes are those of the examples):

Day 1: Polycomplex 2: 2 tablets, 2 times a day,
Day 2: Polycomplex 4: 1 tablet, 3 times a day, +Polycomplex 1: 2 tablets, 2 times a day,
Day 3: Polycomplex 9: 2 tablets, 3 times a day +Polycomplex 8: 2 tablets, 3 times a day,
Day 4: Polycomplex 4: 1 tablet, 3 times a day +Polycomplex 3: 2 tablets, 3 times a day
Day 5: nothing
Day 6: same dosage as Day 1
Day 7: same dosage as Day 2
Day 8: same dosage as Day 3
Day 9: same dosage as Day 4
Day 10: same dosage as Day 5
Etc.

The treatment protocol is presented in the following table:

| | Treatment protocol | | | | | | | | | | | | | | | |
|---|---|---|---|---|---|---|---|---|---|---|---|---|---|---|---|---|
| | Category | | | | | | | | | | | | | | | |
| | 1 | | | | 2 | | | | 1 | | | | 1 | | | |
| | Product | | | | | | | | | | | | | | | |
| | Polycomplex 2 | | | | Polycomplex 4 | | | | Polycomplex 3 | | | | Polycomplex 1 | | | |
| | mg | | | | | | | | | | | | | | | |
| | 2.5 | | | | 0.4 | | | | 0.7 | | | | 2.3 | | | |
| | M | Noon | E | Total | M | Noon | E | Total | M | Noon | E | Total | M | Noon | E | Total |
| Day 1 | 2 | — | 2 | 4 | — | — | — | 0 | — | — | — | 0 | — | — | — | 0 |
| Day 2 | — | — | | 0 | 1 | 1 | 1 | 3 | — | — | — | 0 | 2 | — | 2 | 4 |
| Day 3 | — | — | | 0 | — | — | — | 0 | — | — | — | 0 | — | — | — | 0 |
| Day 4 | — | — | | 0 | 1 | 1 | 1 | 3 | 2 | 2 | 2 | 6 | — | — | — | 0 |
| Day 5 | — | — | | 0 | — | — | — | 0 | — | — | — | 0 | — | — | — | 0 |
| Total tab/month | | 24 | | | | 36 | | | | 36 | | | | 24 | | | |
| Total mg/month | | 48 | | | | 14.4 | | | | 26.2 | | | | 56.2 | | | |

| | | Category | | | | | | | |
|---|---|---|---|---|---|---|---|---|---|
| | | 1 | | | | 2 | | | |
| | | Product | | | | | | | |
| | | Polycomplex 9 | | | | Polycomplex 8 | | | |
| | | mg | | | | | | | |
| | | 0.2 | | | | 0.9 | | | |
| | | M | Noon | E | Total | M | Noon | E | Total | Total tab/day |
| Day 1 | | — | — | — | 0 | — | — | — | 0 | 4 |
| Day 2 | | — | — | — | 0 | — | — | — | 0 | 7 |
| Day 3 | | 2 | 2 | 2 | 8 | 2 | 2 | 2 | 8 | 12 |
| Day 4 | | — | — | — | 0 | — | — | — | 0 | 9 |
| Day 5 | | — | — | — | 0 | — | — | — | 0 | 0 |
| Total tab/month | | | 36 | | | | 36 | | | 192 |
| Total mg/month | | | 7.2 | | | | 36 | | | 186 |
| | | | | | Total AO + Sc (mg) | | | | | 135.6 |
| | | | | | Total FA + AA (mg) | | | | | 50.4 |
| | | | | | AO + Sc/FA + AA ratio | | | | | 2.69 |

Legend:
category =,
tab = tablet,
M = morning,
E = evening,
mg = milligram of polycomplex,
AO = Antioxidants,
FA = Fatty acids,
AA = Amino acids,
Sc = Scavengers (free radical scavengers)

This study was national, multicentric, non-randomized and non-blinded.

The experimental unit was the patient. The factor studied was the ALSQ-40 score.

Two levels of the ALSQ-40 score were defined and compared:

M Score: score determined for each patient during follow-up visits.

R Score: worldwide reference score of disease progression without treatment.

The criteria analyzed and the statistical analysis plan are described below.

—Descriptive Analysis at Inclusion in the Study:
1. Date of birth
2. ALS diagnosis date
3. Age at ALS diagnosis
4. Treatment start date
5. Time between the ALS diagnosis date and treatment start date
6. Sex
7. Overall ALSQ-40 score
8. Time between the date of evaluation of the ALSQ-40 score at inclusion and the treatment start date
9. Score for each item of the ALSQ-40 scale Qualitative variables: strength, percentage, distribution, minimum, $1^{st}$ quartile, median, $3^{rd}$ quartile, maximum.

Quantitative variables: minimum, $1^{st}$ quartile, median, $3^{rd}$ quartile, maximum, mean, standard deviation, 95% confidence interval.

Study of the Visits:
1. Duration of follow-up
2. Number of visits
3. Interval between visits Descriptive analysis: strength, percentage, distribution, minimum, $1^{st}$ quartile, median, $3^{rd}$ quartile, maximum, mean, standard deviation, 95% confidence interval.

Quantitative Study of the ALSQ-40 Score:
1. Comprehensive study of the ALSQ-40 score
2. Overall study of the evolution as a % of the ALSQ-40 score
3. Item/item score of the ALSQ-40 scale
4. Study of the evolution as a % of the ALSQ-40 score based on each item Descriptive analysis: strength, percentage, distribution, minimum, $1^{st}$ quartile, median, $3^{rd}$ quartile, maximum, mean, standard deviation, 95% confidence interval.

Comparative analysis: t test to compare final M and R scores. The equality of variances was verified by means of the Folded F test.

Qualitative Study of the ALSQ-40 Score:
1. Comprehensive study of ALSQ-40 score evolution
2. Study of the evolution based on the items of the ALSQ-40 score Descriptive analysis: strength, percentage, distribution.

Evolution of the data was analyzed using a linear regression model: the following parameters were analyzed for the M and R scores: correlation coefficient $R^2$ and associated P-value, intercept and slope (ax+b).

Comparison of the success/failure rates: $chi^2$ test or Fisher's exact test according to the theoretical strengths obtained by unilateral assumption (% success >% of failure).

This method will be used for the two following studies.

Data Management:

The data were entered manually for each case in individual Excel files.

The coherency of the data was verified. The data were transferred using SAS software (Institute Inc. software version 9) for statistical analysis.

The significance level was set at p=0.05. The conditions of application of the tests used were verified.

Results 21 cases were included in this study.

| | CRITERIA | DESCRIPTION AND COMMENTS | RESULTS |
|---|---|---|---|
| | A-Descriptive analysis at inclusion in the study | | |
| 1. | Date of birth | Median interval corresponding to 57% of the cases studied | 1941-1950 |
| 2. | ALS diagnosis date | Median interval corresponds to 2/3 of cases | 2007-2010 |
| 3. | Age at ALS diagnosis | Median age | 57 |
| 4. | Treatment start date | Median interval corresponding to 48% of the cases studied | 2009-2010 |
| 5. | Time between the ALS diagnosis date and treatment start date | Median time | 15.7 months |
| 6. | Sex | % men | 61.90% |
| 7. | Overall ALSQ-40 score | Median score | 33 |
| | | Mean score | 30 |
| 8. | Time between the date of evaluation of the ALSQ-40 score at inclusion and the treatment start date | Median | −6 days |
| | | Mean time | 45 days |
| 9. | Score for each item of the ALSQ-40 scale | | |
| | a. Speech | Mean. | 3.4 |
| | b. Salivation | The distribution of each item | 3.4 |
| | c. Swallowing | reveals two families: Items A, B, C | 3.5 |
| | d. Writing | and J with a mean of between 3 and | 2.8 |
| | e. Ability to cut food | 4 and the other items have a mean | 2.7 |
| | f. Ability to dress and wash | of between 2 and 3. | 2.5 |
| | g. Ability to roll over in bed | | 2.8 |

| CRITERIA | DESCRIPTION AND COMMENTS | RESULTS |
|---|---|---|
| h. Walking | | 2.5 |
| i. Ability to climb stairs | | 2.3 |
| j. Breathing | | 3.2 |
| B-Study of visits | | |
| 1. Length of follow-up | Median | 665 months i.e., 1.8 years |
| 2. Number of visits | Median number of visits | 7 |
| 3. Interval between visits | Median | 60 days |
| | 77% of the intervals between the visits | <100 days |

Quantitative Study of the ALSQ-40 Score:

a. Comprehensive Study of the ALSQ-40 Score

| Data | Median score of the patients at inclusion | Score of the patients at the end of the study M | Median reference score at the end of the study R |
|---|---|---|---|
| Median | 33 | 17 | 13.8 |
| Mean ± standard deviation | 30.0 ± 8.5 | 19.5 ± 7.9 | 12.3 ± 9.3 |
| 95% CI | [26.1; 33.8] | [15.8; 23.1] | [8.1; 16.6] |
| P-value | | 0.011 | |

Legend: 95% CI = 95% Confidence interval

A statistically significant difference (p=0.011) between the mean scores of the M and R groups was demonstrated.

The mean score of Group M is 19.5 compared to the mean score of group R of 12.3.

Compared to the mean score noted at inclusion the reduction in group M is 35%, in group R this reduction is 59%.

b. Comprehensive Study of the Evolution of the % of the ALSQ-40 Score

| Data | Final score of the patients M/ Inclusion score | Final reference score R/ Inclusion score | % of improvement M Group/ R Group |
|---|---|---|---|
| Median | −35.3% | −55.5% | 20.0% |
| Mean ± standard deviation | −30.5 ± 28.9% | −60.1 ± 30.0% | 29.7 ± 38.8% |
| 95% CI | [−43.6; −18.3] | [−73.8; −46.5] | [12.0; 47.3] |
| P-value | | 0.0022 | |

Legend: 95% CI = 95% Confidence interval

The mean decrease in the ALSQ-40 score in the M group is 30.5%, in the R group this decrease is 60.1%. The improvement of the M group compared to the R group is therefore 29.7%.

This difference is significant (p=0.0022).

c. Item/Item Score of the ALSQ-40 Scale

A statistical analysis of each item making up the ALSQ-40 score was performed. The following table presents the results of the change in each item in the M and R groups.

| Item | Score | Median | Mean ± standard deviation | 95% CI | P-value |
|---|---|---|---|---|---|
| Speech (*) | inclusion | 4.0 | 3.1 ± 1.2 | [2.6; 3.7] | |
| | M | 2.0 | 2.3 ± 1.6 | [1.6; 3.0] | 0.047 |
| | R | 1.5 | 1.5 ± 1.0 | [1.0; 1.9] | |
| Salivation (*) | inclusion | 4.0 | 3.4 ± 0.8 | [3.0; 3.7] | |
| | M | 3.0 | 2.8 ± 1.3 | [2.2; 3.4] | 0.007 |
| | R | 1.6 | 1.5 ± 1.0 | [1.1; 2.0] | |
| Swallowing (*) | inclusion | 4.0 | 3.5 ± 0.6 | [3.3; 3.8] | |
| | M | 3.0 | 3.0 ± 1.0 | [2.5; 3.4] | <0.0001 |
| | R | 1.7 | 1.6 ± 1.0 | [1.2; 2.1] | |
| Writing | inclusion | 3.0 | 2.9 ± 1.0 | [2.4; 3.4] | |
| | M | 2.0 | 1.6 ± 1.4 | [1.0; 2.3] | 0.32 |
| | R | 1.3 | 1.3 ± 1.0 | [0.8; 1.7] | |
| Ability to cut | inclusion | 3.0 | 2.8 ± 1.3 | [2.2; 3.4] | |
| | M | 1.0 | 1.2 ± 1.3 | [0.7; 1.8] | 0.91 |
| | R | 1.3 | 1.2 ± 1.0 | [0.7; 1.7] | |
| Ability to dress | inclusion | 3.0 | 2.6 ± 1.3 | [2.0; 3.2] | |
| | M | 1.0 | 1.0 ± 1.2 | [0.4; 1.5] | 0.93 |
| | R | 0.6 | 1.0 ± 1.1 | [0.5; 1.5] | |
| Ability to roll over | inclusion | 3.0 | 3.0 ± 1.3 | [2.4; 3.5] | |
| | M | 2.0 | 1.7 ± 1.2 | [1.2; 2.3] | 0.20 |
| | R | 1.0 | 1.3 ± 1.1 | [0.8; 1.8] | |
| Walking (*) | inclusion | 3.0 | 2.5 ± 1.0 | [2.0; 3.0] | |
| | M | 2.0 | 1.6 ± 0.8 | [1.2; 1.9] | 0.029 |
| | R | 1.3 | 1.0 ± 0.8 | [0.6; 1.4] | |
| Ability to climb | inclusion | 3.0 | 2.2 ± 1.3 | [1.6; 2.8] | |
| | M | 0.0 | 0.8 ± 1.1 | [0.3; 1.3] | 0.88 |
| | R | 0.6 | 0.9 ± 0.9 | [0.5; 1.3] | |
| Breathing (*) | inclusion | 4.0 | 3.3 ± 1.1 | [2.8; 3.8] | |
| | M | 4.0 | 3.2 ± 1.2 | [2.7; 3.8] | <0.0001 |
| | R | 1.6 | 1.5 ± 1.2 | [1.0; 2.0] | |

(*) Statistically significant items

Legend: 95% CI = 95% Confidence interval

A statistically significant difference (p<0.05) was shown between the mean scores of the M and R groups for the following items: Speech, Salivation, Swallowing, Walking and Breathing. In each case the mean M score is higher than the mean R score.

d. Study of the Evolution of the ALSQ-40 Score Based on Each Item

The following table presents for each of the items the evolution as a percentage of the ALSQ-40 score in the two M and R groups compared to the score at inclusion as well as the evolution as a percentage of the M group compared to the R group.

| Item | | Final M score/ Inclusion score | Final R score/ Inclusion score | % of improvement M Group/R Group | P-value |
|---|---|---|---|---|---|
| Speech (*) | Mean | −29.0 ± 40.0% | −50.8 ± 28.2% | 21.8 ± 26.3% | 0.048 |
| | 95% CI | [−47.2; −10.7] | [−63.6; −37.9] | [9.8; 33.8] | |
| Salivation (*) | Mean | −18.3 ± 29.7% | −54.5 ± 27.2% | 36.3 ± 37.0% | 0.002 |
| | 95% CI | [−31.8; −4.7] | [−66.9; −42.1] | [19.4; 53.1] | |
| Swallowing (*) | Mean | −16.0 ± 26.2% | −53.3 ± 28.2% | 37.3 ± 25.3% | <0.0001 |
| | 95% CI | [−27.9; −4.1] | [−66.1; −40.4] | [25.8; 48.8] | |
| Writing | Mean | −38.9 ± 42.3% | −51.0 ± 32.3% | 12.1 ± 41.7% | 0.30 |
| | 95% CI | [−58.1; −19.6] | [−65.8; −36.3] | [−6.8; 31.1] | |
| Ability to cut | Mean | −51.5 ± 41.8% | −52.8 ± 32.2% | 1.2 ± 45.5% | 0.91 |
| | 95% CI | [−70.6; −32.5] | [−67.4; −38.1] | [−19.5; 21.9] | |
| Ability to dress | Mean | −55.0 ± 52.0% | −57.5 ± 34.5% | 2.5 ± 55.6% | 0.86 |
| | 95% CI | [−78.6; −31.3] | [−73.2; −41.7] | [−22.8; 27.8] | |
| Ability to roll over | Mean | −31.0 ± 47.1% | −52.0 ± 33.2% | 21.0 ± 50.1% | 0.10 |
| | 95% CI | [−52.4; −9.5] | [−67.1; −36.9] | [−1.8; 43.9] | |
| Walking(*) | Mean | −33.0 ± 26.7% | −54.8 ± 33.2% | 21.8 ± 29.8% | 0.024 |
| | 95% CI | [−45.1; −20.8] | [−69.9; −39.7] | [8.2; 35.3] | |
| Ability to climb | Mean | −52.3 ± 54.1% | −51.1 ± 35.4% | −1.2 ± 42.5% | 0.93 |
| | 95% CI | [−77.0; −27.7] | [−67.2; −35.0] | [−20.6; 18.1] | |
| Breathing (*) | Mean | 0 ± 24.3% | −53.1 ± 32.8% | 53.2 ± 33.6% | <0.0001 |
| | 95% CI | [−11.1; 11.1] | [−68.1; −38.3] | [37.9; 68.5] | |

(*) Statistically significant items
Legend: 95% CI = 95% Confidence interval

Qualitative Study of the ALSQ-40 Score:

1. Comprehensive Study

The evolutions of the M and R scores are compared.

If the slope of the M score is positive, the case is considered "improved."

If the slope of the M score is greater than the slope of the R score and lower than 0, the case is considered as "deceleration of the disease."

If the slope of the M score is greater than or equal to the slope of the R score, the case is considered as "degraded."

The evolution was also consolidated to define two classes: "success" and "failure." Improvement and deceleration determine the "success" class, degradation constitutes the "failure" class.

| Evolution of functional capabilities (ALSQ40) | Distribution | | Success/Failure | | P-value |
|---|---|---|---|---|---|
| Improvement | 3 | 14.3% | 16 | 76.2% | 0.0008 |
| Deceleration | 13 | 61.9% | | | |
| Degradation | 5 | 23.8% | 5 | 23.8% | |
| Favorable evolution rate | 21 | | 21 | | |

Study Based on the Items

| Item | Evolution | Distribution | | Success/Failure | | P-value |
|---|---|---|---|---|---|---|
| Speech | Improvement | 1 | 4.8% | 11 | 52.4% | 0.50 |
| | Deceleration | 10 | 47.6% | | | |
| | Degradation | 10 | 47.6% | 10 | 47.6% | |
| Salivation | Improvement | 1 | 4.8% | 13 | 61.9% | 0.11 |
| | Deceleration | 12 | 57.1% | | | |
| | Degradation | 8 | 38.1% | 8 | 38.1% | |
| Swallowing | Improvement | 1 | 4.8% | 12 | 57.2% | 0.27 |
| | Deceleration | 11 | 52.4% | | | |
| | Degradation | 9 | 42.9% | 9 | 42.9% | |
| Writing | Improvement | 0 | 0 | 10 | 47.6% | 0.73 |
| | Deceleration | 10 | 47.6% | | | |
| | Degradation | 11 | 52.4% | 11 | 52.4% | |
| Ability to cut | Improvement | 0 | 0 | 6 | 28.6% | 0.99 |
| | Deceleration | 6 | 28.6% | | | |
| | Degradation | 15 | 71.4% | 15 | 71.4% | |
| Ability to dress | Improvement | 1 | 4.8% | 4 | 19.1% | 1.00 |
| | Deceleration | 3 | 14.3% | | | |
| | Degradation | 17 | 81.0% | 17 | 81.0% | |
| Ability to roll over | Improvement | 2 | 9.6% | 6 | 28.6% | 0.99 |
| | Deceleration | 4 | 19.0% | | | |
| | Degradation | 15 | 71.4% | 15 | 71.4% | |
| Walking | Improvement | 0 | 0 | 6 | 28.6% | 0.99 |
| | Deceleration | 6 | 28.6% | | | |
| | Degradation | 15 | 71.4% | 15 | 71.4% | |
| Ability to climb | Improvement | 2 | 9.6% | 6 | 28.6% | 0.99 |
| | Deceleration | 4 | 19.0% | | | |
| | Degradation | 15 | 71.4% | 15 | 71.4% | |
| Breathing | Improvement | 4 | 19.0% | 11 | 52.4% | <0.0001 |
| | Deceleration | 14 | 66.7% | | | |
| | Degradation | 3 | 14.3% | 3 | 14.3% | |

The Speech, Salivation, Swallowing, Breathing items show a greater than 50% success rate.

A statistically significant difference between the success and failure percentages for the "Breathing" item (p<0.0001) was demonstrated.

—Conclusion of the Study:

The aim was to analyze the results of the retrospective study (21 patients). The aim of this study was to demonstrate the effectiveness of preparations of polycomplexes containing Poly-lysine compounds in volunteer patients with ALS.

The effectiveness factor studied was the ALSQ-40 score: ALS functional progression scale. The score evaluated for each patient during follow-up visits was compared to the theoretical score of disease progression without treatment.

21 cases were included in this study. The descriptive analysis at inclusion showed a high variability of the parameters analyzed.

The study of the visits also revealed great diversity concerning the duration of follow-up, the number of visits as well as the difference between visits.

The comprehensive quantitative study of the ALSQ-40 score showed a statistically significant difference (p=0.0011) between the final mean scores of the M (patients) and R (international reference) groups. The mean score of the M group is 19.5 compared to the mean score of the R group of 12.3.

The improvement of the M group compared to the R group is therefore 29.7%. This difference is significant (p=0.0022).

The item by item analysis showed a statistically significant difference (p<0.05) between the mean scores of the M and R groups for the following items: Speech, Salivation, Swallowing, Walking and Breathing. In each case the mean M score is higher than the mean R score.

The qualitative study of the ALSQ-40 score showed a statistically significant percentage of "success" (p=0.0008). In the case of the item/by item analysis, the Speech, Salivation, Swallowing and Breathing items have a greater than 50% success rate.

A statistically significant difference between the success and failure percentages for the "Breathing" item (p<0.0001) was demonstrated.

Study 3

This study focused on 2 groups treated at different times.

The first group (M1) of 21 cases corresponds to Study 2, and the second group (M2) corresponds to 18 other volunteer patients.

The dosage for this study is as follows (with the understanding that the polycomplexes are administered in compositions with the excipients of the compositions of examples 13 and 14 and that the polycomplexes are those of the examples):

Day 1: Polycomplex 2: 2 tablets, 2 times a day,
Day 2: Polycomplex 10: 2 tablets, 2 times a day +Polycomplex 3: 2 tablets, 2 times a day,
Day 3: Polycomplex 1: 2 tablets, 2 times a day, +Polycomplex 11: 2 tablets, 2 times a day,
Day 4: Polycomplex 11: 3 tablets, 1 time per day +Polycomplex 12: 3 tablets, 1 time per day
Day 5: nothing,
Day 6: same dosage as Day 1,
Day 7: same dosage as Day 2,
Day 8: same dosage as Day 3,
Day 9: same dosage as Day 4,
Day 10: same dosage as Day 5,
Etc.

The treatment protocol is presented in the following table:

| Treatment protocol | | | | | | | | | | | | | | | | |
|---|---|---|---|---|---|---|---|---|---|---|---|---|---|---|---|---|
| Category | | | | | | | | | | | | | | | | |
| 1 | | | | 1 + 2 (50%) | | | | 1 | | | | 1 | | | | |
| Product | | | | | | | | | | | | | | | | |
| Polycomplex 2 | | | | Polycomplex 10 | | | | Polycomplex 3 | | | | Polycomplex 1 | | | | |
| mg | | | | | | | | | | | | | | | | |
| 2.5 | | | | 2 | | | | 0.7 | | | | 2.3 | | | | |
| M | Noon | E | Total | M | Noon | E | Total | M | Noon | E | Total | M | Noon | E | Total | |
| Day 1 | 2 | — | 2 | 4 | — | — | — | 0 | — | — | — | 0 | — | — | — | 0 |
| Day 2 | — | — | — | 0 | 2 | — | 2 | 4 | 2 | — | 2 | 4 | — | — | — | 0 |
| Day 3 | — | — | — | 0 | — | — | — | 0 | — | — | — | 0 | 2 | — | 2 | 4 |
| Day 4 | — | — | — | 0 | — | — | — | 0 | — | — | — | 0 | — | — | — | 0 |
| Day 5 | — | — | — | 0 | — | — | — | 0 | — | — | — | 0 | — | — | — | 0 |
| Total tab/month | | 24 | | | | 24 | | | | 24 | | | | 24 | | |
| Total mg/month | | 48 | | | | 48 | | | | 16.8 | | | | 55.2 | | |

| Category | | | |
|---|---|---|---|
| 2 | | 2 | |
| Product | | | |
| Polycomplex 11 | | Polycomplex 12 | |
| mg | | | |
| 0.6 | | 1.5 | Total |
| M | Noon | E | Total | M | Noon | E | Total | tab/day |
| Day 1 | — | — | — | 0 | — | — | — | 0 | 4 |
| Day 2 | — | — | — | 0 | — | — | — | 0 | 8 |
| Day 3 | 2 | — | 2 | 4 | — | — | — | 0 | 8 |

| Treatment protocol | | | | | | | | | |
|---|---|---|---|---|---|---|---|---|---|
| Day 4 | — | — | 3 | 3 | 3 | — | — | 3 | 8 |
| Day 5 | — | — | — | 0 | — | — | — | 0 | 0 |
| Total tab/month | | 42 | | | 18 | | | | 156 |
| Total mg/month | | 21 | | | 19.62 | | | | 208.62 |
| | | | | | Total AO + Sc (mg) | | | | 144 |
| | | | | | Total FA + AA (mg) | | | | 64.62 |
| | | | | | AO + Sc/FA + AA ratio | | | | 2.23 |

Legend:
tab = tablet,
M = morning,
E = evening,
mg = milligram of polycomplex,
AO = Antioxidants,
FA = Fatty acids,
AA = Amino acids,
Sc = Scavengers (free radical scavengers),
category 1 = AO + Sc,
category 2 = AA + FA Methodology:

This study was national, multicentric, non-randomized and non-blinded.

The experimental unit was the patient.

The factor studied was the ALSQ-40 (ALS functional progression scale) score.

Three ALSQ-40 scores were defined and compared:

M1 Score: score determined for each patient during the second study.

M2 Score: score determined for each patient during the "additional" study.

R2 Score: reference score of the "additional" study.

Criteria Analyzed and Statistical Analysis Plan:

Comprehensive Study of the M1, M2 and R2 ALSQ-40 Scores.

Descriptive Analysis-Comparability of the Groups at Inclusion in the Study (Start of Treatment):
1. Overall ALSQ-40 score,
2. Duration of treatment.

Quantitative variables: minimum, $1^{st}$ quartile, median, $3^{rd}$ quartile, maximum, mean, standard deviation, 95% confidence interval.

Comparative analysis: t test to compare the M1 and M2 scores and the durations of treatment of the two groups. The equality of variances was verified by means of the Folded F test.

Quantitative Study of the ALSQ-40 Score:

Comprehensive Study of the ALSQ-40 Score:

Descriptive analysis: strength, percentage, distribution, minimum, $1^{st}$ quartile, median, $3^{rd}$ quartile, maximum, mean, standard deviation, 95% confidence interval.

Comparative analysis: t test to compare the final M1 and M2 scores. The equality of variances was verified by means of the Folded F test.

Covariance analysis with as co-variable:

ALSQ-40 score at inclusion

Duration of treatment.

Evaluation of the ALSQ-40 M2/R2 Score:

Descriptive analysis: strength, percentage, distribution, minimum, $1^{st}$ quartile, median, $3^{rd}$ quartile, maximum, mean, standard deviation, 95% confidence interval.

Comparative analysis: t test to compare the final M2 and R2 scores. The equality of variances was verified by means of the Folded F test.

The data were entered manually for each case in individual Excel files.

The coherency of the data was verified. The data were transferred by SAS software (Institute Inc. software version 9) for statistical analysis.

The significance level was set at p=0.05. The conditions of application of the tests used were verified.

Results

Descriptive Analysis-Comparison of the Groups at Inclusion in the Study:

Inclusion in the study of the different cases corresponds to the date of evaluation closest to the treatment start date.

Overall ALSQ-40 Score

| Data | Group M1 | Group M2 |
|---|---|---|
| Number of patients | 21 | 18 |
| Median of the score at inclusion | 33.0 | 33.5 |
| Mean ± standard deviation | 30.0 ± 8.5 | 32.8 ± 5.6 |
| 95% CI | [26.1; 33.8] | [30.0; 35.6] |
| P-value | 0.24 | |

Legend: 95% CI = 95% Confidence interval

No statistically significant difference was shown between the mean scores at inclusion between the two groups M1 and M2 (p=0.24).

Duration of Treatment (in Days)

| Data | Group M1 | Group M2 |
|---|---|---|
| Number of patients | 21 | 18 |
| Median of the durations of treatment | 665 | 645 |

-continued

| Data | Group M1 | Group M2 |
|---|---|---|
| Mean ± standard deviation | 908 ± 798 | 747 ± 505 |
| 95% CI | [545; 1271] | [496; 998] |
| P-value | | 0.47 |

Legend: 95% CI = 95% Confidence interval

No statistically significant difference was shown between the mean scores at inclusion between the two groups M1 and M2 (p=0.47).

Quantitative Study of the ALSQ-40 Score after the Period of Treatment:

Comprehensive Study of the ALSQ-40 Score

The distribution variables of the mean ALSQ-40 score of M1 and M2 groups at final evaluation.

| Data | Group M1 | Group M2 |
|---|---|---|
| Number of patients | 21 | 18 |
| Median of the scores at final evaluation | 17 | 26 |
| Mean ± standard deviation | 19.5 ± 7.9 | 25.4 ± 7.1 |
| 95% CI | [15.8; 23.1] | [21.9; 29.0] |
| P-value adjusted to the score at inclusion | | 0.035 |
| P-value adjusted to the length of treatment | | 0.014 |

Legend: 95% CI = 95% Confidence interval

A statistically significant difference (p=0.035 adjusted to the score at inclusion and p=0.014 adjusted to the duration of treatment) was shown between the mean scores of M1 and M2 groups. The mean score of the M1 group is 19.5 compared to the mean score of M2 group of 25.4.

Comprehensive Study of the ALSQ-40 M2 Score Versus R2 Score

The distribution variables of the mean ALSQ-40 M2 and R2 score at final evaluation.

| Data | Score at inclusion | Final M2 score | Final R2 score |
|---|---|---|---|
| Number of patients | 18 | 18 | 18 |
| Median of the scores | 33 | 26 | 15.3 |
| Mean ± standard deviation | 32.8 ± 5.6 | 25.4 ± 7.1 | 15.6 ± 8.9 |
| 95% CI | [30.0; 35.6] | [21.9; 29.0] | [11.1; 20.0] |
| P-value | | 0.0008 | |

Legend: 95% CI = 95% Confidence interval

A statistically significant difference (p=0.0008) between the mean M2 and R2 scores was demonstrated. The mean M2 score is 25.4 compared to the mean R2 score of 15.6.

Compared to the mean score noted at inclusion, the decrease in the M2 score is 23%, the decrease in the R2 score is 52%.

Study of the Evolution of the ALSQ-40 M2/R2 Score

The following table presents as a percentage the ALSQ-40 score in the two groups M2 and R2 compared to the score at inclusion, as well as the evolution as a percentage between group M2 compared to group R2.

| Data | Final M2 score/ Inclusion score | Final R2 score/ Inclusion score | % of improvement M2 Group/ R2 Group |
|---|---|---|---|
| Number of patients | 18 | 18 | 18 |
| Median of the percentages | −10.0% | −55.0% | 23.7% |
| Mean ± standard deviation | −20.3 ± 24.3% | −52.4 ± 28.9% | 32.1 ± 33.8% |
| 95% CI | [−32.4; −8.2] | [−66.8; −38.0] | [15.3; 48.9] |
| P-value | | 0.0010 | |

Legend: 95% CI = 95% Confidence interval

The mean decrease in the M2 score is 20.3%, the R2 score decreases by 52.4%. The improvement of the M2 score compared to R2 score is therefore 32.1%. This difference is significant (p=0.0010).

Conclusion

The aim of this study was to compare the effectiveness of two treatments in volunteer patients with ALS.

The effectiveness factor studied was the ALSQ-40 score: ALS functional progression scale.

39 cases were included in this study. The comparability of the groups did not reveal any statistical difference between the two groups.

The comprehensive quantitative study of the ALSQ-40 score showed a statistically significant difference (p<0.05) between the final mean scores of the M1 and M2 groups. The mean score of the M1 group is 19.5 compared to the mean score of the M2 group of 25.4.

The mean decrease in the M2 score is 20.3%, the R2 score decreases by 52.4%. The improvement of the M2 score compared to the R2 score is 32.1%. This difference is significant (p=0.0010).

Study 4

The aim of this study was to demonstrate the effectiveness of preparations of polycomplexes containing Poly-lysine compounds in 31 volunteer patients with ALS.

The dosage for this study is as follows (with the understanding that the polycomplexes are administered in compositions with the excipients of the compositions of examples 13 and 14 and that the polycomplexes are those of the examples):

Day 1: Polycomplex 2: 2 tablets, 3 times a day,

Day 2: Polycomplex 3: 2 tablets, 2 times a day +Polycomplex 5: 2 tablets, 3 times a day, Day 3: Polycomplex 1: 2 tablets, 3 times a day, Day 4: Polycomplex 2: 2 tablets, 3 times a day +Polycomplex 5: 2 tablets, 3 times a day, Day 5: nothing, Day 6: same dosage as Day 1, Day 7: same dosage as Day 2, Day 8: same dosage as Day 3, Day 9: same dosage as Day 4, Day 10: same dosage as Day 5, Etc.

The treatment protocol is presented in the following table:

| | Treatment protocol | | | | | | | | | | | | | | | | |
|---|---|---|---|---|---|---|---|---|---|---|---|---|---|---|---|---|---|
| | Category | | | | | | | | | | | | | | | | |
| | 1 | | | | 1 | | | | 1 | | | | 2 | | | | |
| | | | | | | | | Product | | | | | | | | | |
| | Polycomplex 2 | | | | Polycomplex 3 | | | | Polycomplex 1 | | | | Polycomplex 5 | | | | |
| | | | | | | | | | mg | | | | | | | | |
| | 2.5 | | | | 0.7 | | | | 2.3 | | | | 0.8 | | | | |
| | M | Noon | E | Total | M | Noon | E | Total | M | Noon | E | Total | M | Noon | E | Total | Total |
| Day 1 | 2 | 2 | 2 | 6 | — | — | — | 0 | — | — | — | 0 | — | — | — | 0 | 6 |
| Day 2 | — | — | — | 0 | 2 | — | 2 | 4 | — | — | — | 0 | 2 | 2 | 2 | 6 | 10 |
| Day 3 | — | — | — | 0 | — | — | — | 0 | 2 | 2 | 2 | 6 | — | — | — | 0 | 6 |
| Day 4 | 2 | 2 | 2 | 6 | — | — | — | 0 | — | — | — | 0 | 2 | 2 | 2 | 6 | 12 |
| Day 5 | — | — | — | 0 | — | — | — | 0 | — | — | — | 0 | — | — | — | 0 | 0 |
| Total tab/month | | 72 | | | | 24 | | | | 36 | | | | 72 | | | 204 |
| Total mg/month | | 144 | | | | 16.8 | | | | 82.8 | | | | 57.6 | | | 301.2 |
| | | | | | | | | | | | | Total mg AO + Sc | | | | | 243.6 |
| | | | | | | | | | | | | Total FA + AA | | | | | 57.6 |
| | | | | | | | | | | | | AO + Sc/FA + AA ratio | | | | | 4.23 |

Legend:
tab = tablet,
M = morning,
E = evening,
mg = milligram of polycomplex,
AO = Antioxidants,
FA = Fatty acids,
AA = Amino acids,
Sc = Scavengers (free radical scavengers),
category 1 = AO + Sc,
category 2 = AA + FA Methodology: identical to that of Study 3
Criteria analyzed and statistical analysis plan: identical to those of Study 3
Data management: identical to that of Study 3
Results:

| CRITERIA | DESCRIPTION AND COMMENTS | RESULTS |
|---|---|---|
| A. Descriptive analysis at inclusion in the study | | |
| 1. Date of birth | Median interval corresponding to 45% of the cases studied | 1941-1950 |
| 2. ALS diagnosis date | Median interval corresponds to 70% of the cases | 2007-2010 |
| 3. Age at ALS diagnosis | Median age | 59 |
| 4. Treatment start date | Median interval corresponding to 42% of the cases studied | 2011-2013 |
| 5. Sex | % of men | 64.50% |
| Time between the ALS diagnosis date and treatment start date | Median time | 18.3 months |
| 6. Overall ALSQ-40 score | Median score | 33 |
| | Mean score | 30.50 |
| 7. Time between the date of evaluation of the ALSQ-40 score at inclusion and the treatment start date | Median | −10 days |
| | Mean time | −17 days |
| 8. Score for each item of the ALSQ-40 scale | | |
| a. Speech | Mean. | 3.5 |
| b. Salivation | The distribution of each item reveals | 3.7 |
| c. Swallowing | two families: Items A, B, C and J with a | 3.6 |
| d. Writing | mean of between 3 and 4 and the other | 2.6 |
| e. Ability to cut food | items have a mean of between 2 and 3. | 2.8 |
| f. Ability to dress and wash | | 2.6 |

| CRITERIA | DESCRIPTION AND COMMENTS | RESULTS |
|---|---|---|
| g. Ability to roll over in bed | | 2.9 |
| h. Walking | | 2.6 |
| i. Ability to climb stairs | | 2.4 |
| j. Breathing | | 3.3 |
| B. Study of visits | | |
| 1. Duration of follow-up | Median | 685 months i.e., 1.9 years |
| 2. Number of visits | Median number of visits | 8 |
| 3. Interval between visits | Median | 71 days |
| | 69% of the intervals between visits | <100 days |

C. Quantitative Study of the ALSQ-40 Score
a. Comprehensive Study of the ALSQ-40 Score

| Data | Median score at inclusion of the patients group M | Final median score M group | Final median reference score R |
|---|---|---|---|
| Median of the scores | 33 | 18 | 12.3 |
| Mean ± standard deviation | 30.6 ± 7.9 | 19.8 ± 9.4 | 11.7 ± 9.6 |
| 95% CI | [27.7; 33.5] | [16.3; 23.2] | [8.2; 15.2] |
| P-value | | | 0.0013 |

Legend: 95% CI = 95% Confidence interval

A statistically significant difference (p=0.0013) was demonstrated between the mean scores of the M and R groups. The mean score of the M group is 19.8 compared to the mean score of the R group of 11.7.

Compared to the mean score noted at inclusion, the decrease in group M is 35%, in group R this decrease is 62%.

b. Study of the Evolution of the ALSQ-40 Score

| Data | Final M score/ Inclusion score | Final R score/ Inclusion score | % of improvement Group M/Group R |
|---|---|---|---|
| Median of the percentages | −28.6% | −61.6% | 16.3% |
| Mean ± standard deviation | −32.0 ± 30.8% | −62.8 ± 29.9% | 30.8 ± 36.2% |
| 95% CI | [−43.3; −20.7] | [−73.8; −51.8] | [17.5; 44.1] |
| P-value | | 0.0002 | |

Legend: 95% CI = 95% Confidence interval

The average decrease in the ALSQ-40 score in group M is 32.0%, in group R this decrease is 62.8%. The improvement of group M compared to group R is therefore 30.8%. This difference is significant (p=0.0002).

D. Evolution of Each Item of the ALSQ-40 Scale

| Item | M and R scores at inclusion | Median of the M and R scores | Mean ± standard deviation | 95% CI | P-value |
|---|---|---|---|---|---|
| Speech | inclusion | 3.0 | 2.9 ± 1.4 | [2.4; 3.4] | |
| | M | 2.5 | 2.3 ± 1.7 | [1.7; 2.9] | 0.0033 |
| | R | 1.3 | 1.2 ± 1.1 | [0.8; 1.6] | |
| Salivation | inclusion | 4.0 | 3.3 ± 0.9 | [3.0; 3.6] | |
| | M | 3.0 | 2.6 ± 1.4 | [2.1; 3.2] | 0.0001 |
| | R | 1.3 | 1.3 ± 1.1 | [1.0; 1.7] | |
| Swallowing | inclusion | 4.0 | 3.4 ± 0.9 | [3.0; 3.7] | |
| | M | 3.0 | 2.8 ± 1.3 | [2.4; 3.3] | <0.0001 |
| | R | 1.8 | 1.4 ± 1.1 | [1.0; 1.8] | |
| Writing | inclusion | 3.0 | 2.9 ± 1.0 | [2.5; 3.2] | |
| | M | 3.0 | 1.8 ± 1.6 | [1.2; 2.4] | 0.038 |
| | R | 0.8 | 1.1 ± 1.1 | [0.7; 1.5] | |
| Ability to cut | inclusion | 3.0 | 2.6 ± 1.3 | [2.2; 3.1] | |
| | M | 1.0 | 1.5 ± 1.3 | [1.0; 2.0] | 0.067 |
| | R | 0.3 | 0.9 ± 1.0 | [0.5; 1.3] | |
| Ability to dress | inclusion | 3.0 | 2.6 ± 1.2 | [2.1; 3.0] | |
| | M | 1.0 | 1.3 ± 1.2 | [0.8; 1.7] | 0.31 |
| | R | 0.7 | 1.0 ± 1.1 | [0.6; 1.3] | |
| Ability to roll over | inclusion | 3.0 | 3.0 ± 1.3 | [2.5; 3.4] | |
| | M | 2.0 | 2.0 ± 1.5 | [1.4; 2.5] | 0.031 |
| | R | 1.0 | 1.2 ± 1.2 | [0.7; 1.6] | |
| Walking | inclusion | 3.0 | 2.6 ± 0.9 | [2.3; 2.9] | |
| | M | 2.0 | 1.7 ± 1.1 | [1.3; 2.1] | 0.0061 |
| | R | 0.8 | 1.0 ± 1.0 | [0.6; 1.3] | |
| Ability to climb | inclusion | 3.0 | 2.2 ± 1.3 | [1.7; 2.7] | |
| | M | 1.0 | 1.1 ± 1.2 | [0.7; 1.6] | 0.32 |
| | R | 0.5 | 0.9 ± 1.0 | [0.5; 1.2] | |
| Breathing | inclusion | 3.0 | 3.1 ± 1.2 | [2.7; 3.6] | |
| | M | 3.0 | 2.7 ± 1.4 | [2.2; 3.2] | <0.0001 |
| | R | 1.3 | 1.3 ± 1.2 | [0.9; 1.7] | |

Legend: 95% CI = 95% Confidence interval

A statistically significant difference (p<0.05) was shown between the mean scores of groups M and R for the following items: Speech, Salivation, Swallowing, Writing, Ability to roll over, Walking and Breathing. In each case the mean M score is higher than the mean R score.

E. Evolution of Each Item of the ALSQ-40

The table below presents for each item the evolution of the percentages in the M and R groups. The percentage is obtained by the ratio within the groups of the scores at inclusion and of the final scores.

Percentages of the ratios of scores

| Item | | M Group Final scores/ Scores at inclusion | R Group Final scores/ Scores at inclusion | % of improvement Group M/ Group R | P-value |
|---|---|---|---|---|---|
| Speech (*) | Mean | −24.8 ± 39.2% | −55.7 ± 32.5% | 30.9 ± 29.0% | 0.0013 |
| | 95% CI | [−39.2; −10.5] | [−67.6; −43.8] | [20.2; 41.5] | |
| Salivation (*) | Mean | −21.5 ± 35.3% | −60.2 ± 29.2% | 38.7 ± 39.0% | <0.0001 |
| | 95% CI | [−34.4; −8.6] | [−71.0; −49.5] | [24.4; 53.1] | |
| Swallowing (*) | Mean | −16.9 ± 30.4% | −56.6 ± 32.4% | 39.7 ± 33.8% | <0.0001 |
| | 95% CI | [−28.1; −5.8] | [−68.5; −44.7] | [27.3; 52.1] | |
| Writing | Mean | −35.2 ± 48.9% | −59.7 ± 32.9% | 24.4 ± 48.4% | 0.025 |
| | 95% CI | [−53.1; −17.3] | [−71.7; −47.6] | [6.7; 42.2] | |
| Ability to cut | Mean | −38.8 ± 42.0% | −63.9 ± 33.1% | 25.1 ± 45.2% | 0.011 |
| | 95% CI | [−54.2; −23.4] | [−76.0; −51.8] | [8.5; 41.7] | |
| Ability to dress | Mean | −44.5 ± 47.9% | −59.9 ± 34.8% | 15.4 ± 53.9% | 0.15 |
| | 95% CI | [−62.1; −26.9] | [−72.7; −47.1] | [−4.4; 35.2] | |
| Ability to roll over | Mean | −27.8 ± 47.0% | −55.9 ± 35.0% | 28.0 ± 45.8% | 0.010 |
| | 95% CI | [−45.1; −10.6] | [−68.7; −43.0] | [11.2; 44.8] | |
| Walking (*) | Mean | −30.1 ± 34.8% | −61.5 ± 33.9% | 31.4 ± 35.4% | 0.0007 |
| | 95% CI | [−42.9; −17.3] | [−73.9; −49.0] | [18.4; 44.4] | |
| Ability to climb | Mean | −38.4 ± 49.1% | −56.4 ± 37.7% | 17.9 ± 49.7% | 0.11 |
| | 95% CI | [−56.4; −20.4] | [−70.2; −42.5] | [−0.3; 36.1] | |
| Breathing (*) | Mean | −10.2 ± 28.8% | −56.0 ± 34.2% | 45.8 ± 38.1% | <0.0001 |
| | 95% CI | [−20.8; 0.3] | [−68.6; −43.5] | [31.8; 59.8] | |

(*) Statistically significant items Legend: 95% CI = 95% Confidence interval

F. Qualitative Study of the ALSQ-40 Scores a. Comprehensive Study

| Evolution of functional capacities (ALSQ40) | Breakdown of the patients | | % Success/Failure | | P-value |
|---|---|---|---|---|---|
| Improvement | 4 | 12.9% | 26 | 83.9% | <0.0001 |
| Deceleration | 22 | 71.0% | | | |
| Degradation | 5 | 16.1% | 5 | 16.1% | |
| Total | 31 | | 31 | | | b. Study Based on the Items

| Item | Evolution | Breakdown of the patients | | % Success/Failure | | P-value |
|---|---|---|---|---|---|---|
| Speech | Improvement | 1 | 3.2% | 18 | 58.1% | 0.20 |
| | Deceleration | 17 | 54.8% | | | |
| | Degradation | 13 | 41.9% | 13 | 41.9% | |
| Salivation | Improvement | 1 | 3.2% | 19 | 61.3% | 0.075 |
| | Deceleration | 18 | 58.1% | | | |
| | Degradation | 12 | 38.7% | 12 | 38.7% | |
| Swallowing | Improvement | 1 | 3.2% | 19 | 61.3% | 0.075 |
| | Deceleration | 18 | 58.1% | | | |
| | Degradation | 12 | 38.7% | 12 | 38.7% | |
| Writing | Improvement | 1 | 3.2% | 18 | 58.1% | 0.20 |
| | Deceleration | 17 | 54.8% | | | |
| | Degradation | 13 | 41.9% | 13 | 41.9% | |
| Ability to cut | Improvement | 0 | 0.0% | 14 | 45.2% | 0.45 |
| | Deceleration | 14 | 45.2% | | | |
| | Degradation | 17 | 54.8% | 17 | 54.8% | |
| Ability to dress | Improvement | 2 | 6.5% | 10 | 32.3% | 0.0052 |
| | Deceleration | 8 | 25.8% | | | |
| | Degradation | 21 | 67.7% | 17 | 67.7% | |
| Ability to roll over | Improvement | 3 | 9.7% | 13 | 41.9% | 0.20 |
| | Deceleration | 10 | 32.2% | | | |
| | Degradation | 18 | 58.1% | 18 | 58.1% | |
| Walking | Improvement | 0 | 0.0% | 14 | 45.2% | 0.45 |
| | Deceleration | 14 | 45.2% | | | |
| | Degradation | 17 | 54.8% | 17 | 54.8% | |
| Ability to climb | Improvement | 2 | 6.5% | 13 | 41.9% | 0.20 |
| | Deceleration | 11 | 35.5% | | | |
| | Degradation | 18 | 51.8% | 18 | 51.8% | |
| Breathing | Improvement | 3 | 9.7% | 22 | 71.0% | 0.0010 |
| | Deceleration | 19 | 61.3% | | | |
| | Degradation | 9 | 29.0% | 9 | 29.0% | |

The Speech, Salivation, Swallowing and Breathing items show a greater than 50% success rate. A statistically significant difference between the success and failure percentages for the "Ability to dress" and "Breathing" items (p<0.05) was demonstrated.

Conclusion

The aim of this study was to analyze the effectiveness of preparations of polycomplexes containing Poly-lysine compounds in volunteer patients with ALS.

The effectiveness factor studied was the ALSQ-40 score: ALS functional progression scale. The score evaluated for each patient during follow-up visits was compared to the theoretical score of disease progression without treatment.

31 cases were included in this study. The descriptive analysis at inclusion showed a high variability of the parameters analyzed.

The study of the visits also revealed great diversity concerning the duration of follow-up, the number of visits as well as the time between visits.

The comprehensive quantitative study of the ALSQ-40 score showed a statistically significant difference (p=0.0013) between the final mean scores of the M and R groups.

The mean score of the M group is 19.8 compared to the mean score of the R group equal to 11.7.

The improvement of the M group compared to the R group is therefore 30.8%. This difference is significant (p=0.0002).

The item by item analysis showed a statistically significant difference (p<0.05) between the mean scores of the M and R groups for the following items: Speech, Salivation, Swallowing, Writing, Ability to roll over, Walking and Breathing. In each case the mean M score is higher than the mean R score.

The qualitative study of the ALSQ-40 score showed a statistically significant percentage of "success" (p<0.0001). In the case of the item/by item analysis, the Speech, Salivation, Swallowing and Breathing items have a greater than 50% success rate.

A statistically significant difference between the success and failure percentages for the "Ability to dress" and "Breathing" items (p<0.05) was demonstrated.

The invention claimed is:

1. A composition comprising at least two polycomplexes:
    a first polycomplex composed exclusively of the following Poly-lysine compounds:
    Cysteine-Glutaric Anhydride-Poly-lysine;
    Cysteine-Reduced Glutaraldehyde-Poly-lysine;
    Taurine-Glutaric Anhydride-Poly-lysine;
    Taurine-Reduced Glutaraldehyde-Poly-lysine;
    Methionine-Glutaric Anhydride-Poly-lysine;
    Methionine-Reduced Glutaraldehyde-Poly-lysine;
    Glutathione-Reduced Glutaraldehyde-Poly-lysine;
    Thioctic acid-Poly-lysine
    and
    a second polycomplex consisting of the following Poly-lysine compounds:
    Lauric acid-Poly-lysine;
    Lactic acid-Poly-lysine;
    Pyruvic acid-Poly-lysine.

2. The composition according to claim 1, characterized in that the polycomplex(es) comprising antioxidants and/or free radical scavengers are present in a quantity at least 2.5 times higher by weight than the other polycomplexes.

3. The composition of claim 1, wherein the polycomplex characterized in that the concentration of each of said small molecules in each polycomplex is between $6 \cdot 10^{-5}$ M and $1 \cdot 10^{-4}$ M.

4. The composition according to claim 1 for its use as medication.

5. A method of prevention or treatment of Amyotrophic Lateral Sclerosis (ALS), the method comprising administering to a patient the composition of claim 1.

* * * * *